US011626191B1

(12) United States Patent
Gartner

(10) Patent No.: US 11,626,191 B1
(45) Date of Patent: Apr. 11, 2023

(54) SECURE AND EFFICIENT LABORATORY DIAGNOSIS AND REPORTING

(71) Applicant: Affirmativ Diagnostics PLLC, Bellingham, WA (US)

(72) Inventor: Fritz Gartner, Houston, TX (US)

(*) Notice: Subject to any disclaimer, the term of this patent is extended or adjusted under 35 U.S.C. 154(b) by 0 days.

(21) Appl. No.: 17/903,014

(22) Filed: Sep. 5, 2022

(51) Int. Cl.
| | |
|---|---|
| *G06F 17/00* | (2019.01) |
| *G06F 12/00* | (2006.01) |
| *G06Q 10/06* | (2012.01) |
| *G16H 10/40* | (2018.01) |
| *G16B 30/00* | (2019.01) |
| *G16B 50/00* | (2019.01) |
| *G16H 15/00* | (2018.01) |

(52) U.S. Cl.
CPC ............ *G16H 10/40* (2018.01); *G16B 30/00* (2019.02); *G16B 50/00* (2019.02); *G16H 15/00* (2018.01)

(58) Field of Classification Search
CPC ........ G16H 10/40; G16H 15/00; G16B 30/00; G16B 50/00
See application file for complete search history.

(56) References Cited

U.S. PATENT DOCUMENTS

| | | | |
|---|---|---|---|
| 5,876,926 A | 3/1999 | Beecham | |
| 7,158,979 B2* | 1/2007 | Iverson | ............... G06F 21/6254 707/999.1 |
| 7,516,351 B2 | 4/2009 | Inami et al. | |

(Continued)

FOREIGN PATENT DOCUMENTS

| | | |
|---|---|---|
| EP | 3063299 B1 | 2/2019 |
| WO | WO2004079328 A2 | 9/2004 |
| WO | WO2005109238 A2 | 11/2005 |

OTHER PUBLICATIONS

Agrawal et al., Information Sharing Across Private Databases, IBM Research Center, Jun. 12, 2003, all pages, <https://www.cs.cornell.edu/aevf/research/SIGMOD_2003.pdf>, San Diego, California, USA.

(Continued)

*Primary Examiner* — Maroun P Kanaan
(74) *Attorney, Agent, or Firm* — John J. Bamert, Esq.; Bamert Regan PLLC

(57) ABSTRACT

Embodiments are directed toward facilitating securely and efficiently providing medical-test results. Some embodiments enable secure and efficient mass testing by eliminating the requirement that patients provide personally identifying information after collection of their first testing specimen. The system enables delivering test results to such patients without the patients providing personally identifying information with specimens to be tested. The first time that a patient requests a medical test on a specimen, values representative of biometric characteristic thereof are recorded with personal information for the patient. Some embodiments facilitate looking up the patient's personal information by using values representative of biometrics obtained from the patient's subsequent specimens to be medically tested. Some embodiments facilitate security by storing personal information and biometric identifiers in separate data stores and linking records in those data stores by way of an identifier that does not identify the patient.

20 Claims, 10 Drawing Sheets

(56) References Cited

U.S. PATENT DOCUMENTS

| | | | |
|---|---|---|---|
| 8,676,509 B2 | 3/2014 | De La Torre-Bueno | |
| 9,117,024 B2 | 8/2015 | De La Torre-Bueno | |
| 9,633,176 B2* | 4/2017 | De La Torre-Bueno | ................... G16H 10/40 |
| 9,659,153 B2 | 5/2017 | De La Torre-Bueno | |
| 10,510,437 B2 | 12/2019 | Efros et al. | |
| 2003/0073124 A1 | 4/2003 | Bowman et al. | |
| 2004/0185481 A1 | 9/2004 | Numajiri | |
| 2007/0078871 A1 | 4/2007 | Iverson et al. | |
| 2008/0195326 A1 | 8/2008 | Munzer et al. | |
| 2009/0227897 A1 | 9/2009 | Wendt et al. | |
| 2013/0071847 A1 | 3/2013 | Burnett et al. | |
| 2016/0292393 A1 | 10/2016 | Balwani | |
| 2017/0220775 A1 | 8/2017 | De La Torre-Bueno | |
| 2017/0308680 A1 | 10/2017 | Efros et al. | |
| 2018/0300455 A1 | 10/2018 | Smith et al. | |

OTHER PUBLICATIONS

Ahn, Whose Genome Is It Anyway?: Re-identification and Privacy Protection in Public and Participatory Genomics, 2015, all pages, <https://heinonline.org/HOL/LandingPage?handle=hein.journals/sanlr52&div=22&id=&page=> unknown publication location.

Hart et al., Ten Simple Rules for Digital Data Storage, Oct. 20, 2016, all pages, <https://doi.org/10.1371/journal.pcbi.1005097>, unknown publication location.

Swede et al., National population-based biobanks for genetic research, Genetics in Medicine, Mar. 2007, all pages, <https://www.nature.com/articles/gim200726>, unknown publication location.

Takai-Igarashi et al., Security controls in an integrated Biobank to protect privacy in data sharing: rationale and study design, BMC Medical Informatics and Decision Making, Jul. 6, 2017, all pages, <https://www.researchgate.net/publication/318252811_Security_controls_in_an_integrated_Biobank_to_protect_privacy_in_data_sharing_Rationale_and_study_design>, unknown publication location.

* cited by examiner

SECURE AND EFFICIENT LABORATORY DIAGNOSIS AND REPORTING

FIELD OF THE INVENTION

The invention relates generally to providing laboratory diagnosis and, more particularly, to secure and efficient provision of laboratory diagnosis based on biological specimens.

BACKGROUND OF THE INVENTION

Widespread testing has been shown to be an effective mechanism for preventing, detecting, and controlling the spread of communicable diseases. At-home tests or on-site tests are convenient and simple at a small scale because, unlike laboratory tests, at-home or on-site tests do not require transporting and tracking the biological specimen to be tested in the laboratory along with storing and tracking personally identifiable information, but laboratory testing is often significantly more accurate and thus trustworthy. Moreover, laboratory testing is more appropriate at large scale such as in an enterprise environment because laboratory testing eliminates the need for storing mass quantities of testing equipment, training and maintaining education of personnel to conduct the testing, and disposing of mass quantities of biological material at the location of the enterprise. Laboratory testing would therefore work best if it could be performed efficiently and at scale so that public health authorities or other organizations (e.g., schools, factories, transport centers, or others) can obtain accurate and timely data about the progress of the disease through the local population. In addition, widespread, laboratory testing increases the accurate information provided to individuals regarding their own health and the responsive actions that they can take when they find that they have become infected with or exposed to the disease.

Typical laboratory testing procedures and systems require each patient to provide detailed personal information with each biological specimen collected for testing. Patients are typically required to engage in the time-consuming task of filling out patient intake forms each time they provide a biological specimen for such a test. In addition to the inefficient and time-consuming intake process for each laboratory test, illegible handwriting or data-entry errors may lead to data mismatch or failures to return test results to their associated patient. Accordingly, typical laboratory testing procedures and systems impose significant inefficiency and sources of errors, and such inefficiency and errors preclude efficient and accurate mass testing. These and other related problems reduce the number of enterprises who participate in mass testing.

There are no known solutions, individually or in combination, that facilitate accurate mass testing of many people on a frequent basis with the efficiency and security demanded by enterprises who could internally implement mass testing on a large scale for pandemic prevention, detection, or control. For example, U.S. Pre-Grant Publication No. 2004/0185481 issued to Numajiri teaches assisting with long-term planning of an individual patient's healthcare plan by using the patient's DNA to look up prior test results that may assist with such planning in combination with the result of a current test (see paragraphs 0044 and 0046), but Numajiri is not directed toward efficient mass testing and thus fails to teach efficient accessioning for the current test, let alone addressing the security problems associated with mass testing or gathering personally identifiable information.

As another example, European Patent No. EP3063299 issued to Martine et al. ("Martine") and U.S. Pre-Grant Publication No. 2013/0071847 issued to Burnett et al. ("Burnett") teach identifying a dog that defecated in public by sequencing DNA in such stool to send a warning to the owner of the dog, but Martine and Burnett are not directed toward conducting medical tests and thus fail to teach accessioning the stool for medical testing, let alone addressing the security problems involved with tracking the stool throughout the medical test or gathering information for medical purposes.

As yet another example, U.S. Pat. No. 5,876,926 issued to Beecham teaches using a biometric sample to retrieve test results from a test on a previously provided biometric sample, but Beecham is not directed toward efficient mass testing and thus fails to teach efficient accessioning for the current test to enable proactive notification to the patient without further action being required of the patient after the test is conducted, let alone addressing the security problems associated with mass testing or gathering personally identifiable information.

As a further example, U.S. Pre-Grant Publication No. 2009/0227897 issued to Wendt et al. ("Wendt") teaches using DNA correlation to confirm patient identification after the patient has been identified but before providing the test results as an alternative mechanism for identification confirmation, but Wendt is not directed toward efficient mass testing and thus fails to teach efficient accessioning for the current test to enable notification of the test result to the patient without further action being required of the patient after the test is conducted, let alone addressing the security problems associated with mass testing or gathering personally identifiable information.

As yet a further example, U.S. Pre-Grant Publication No. 2017/0308680 issued to Efros et al. ("Efros") teaches evaluating whether a candidate is eligible to participate in a clinical trial based on prior or concurrent involvement in other trials (see paragraph 0033) and de-identifying the candidates and participants to avoid the complications involved with gathering personally identifiable information in connection with medical testing (see paragraph 0026), but clinical trials serve a research purpose that lacks a need for identifying participants as opposed to providing patients with results of their individual medical tests. Accordingly, Efros fails to teach efficient accessioning that permits providing test results to patients, let alone addressing the securing problems involved with gathering personally identifiable information.

As another example, U.S. Pat. No. 7,158,979 issued to Iverson et al. ("Iverson") teaches de-identifying individually identifiable information to enable use of the de-identified information for research purposes (see line 55 of column 3 through line 11 of column 5), but such research purposes lack a need for identifying individuals as opposed to providing patients with results of their individual medical tests. Accordingly, Iverson fails to teach efficient accessioning that permits providing test results to patients in a secure manner.

As a further example, U.S. Pre-Grant Publication No. 2016/0292393 issued to Balwani teaches providing a patient with a first identifier that the patient can use to access test results without providing personal information, but handing out such identifiers and tasking the patient with properly storing, remembering, or maintaining the identifier until the test result is available introduces significant challenges and opportunity for error (e.g., handing out the wrong identifier or losing the identifier) when conducting mass testing at scale. U.S. Pre-Grant Publication Nos. 2008/0195326, 2009/0227897, 2017/0220775, and 2018/0300455 and U.S. Pat. No. 7,516,351 teach testing procedures that introduce similar problems that preclude use of such procedures at scale.

As another example, International Application Publication No. WO 2004/079328 issued to Intresco B.V. ("Intresco") teaches a method for restoring lost, outdated, deleted, or otherwise unusable personally identifiable information of a donor of a biological sample by making a public call to all prior donors to request the donors to respond with their personally identifying information along with a new biological sample to facilitate matching a donor with the original biological sample and thereby restoring the dataset (see Abstract and p. 7, lines 3-15), but Intresco is not directed toward efficient mass testing and thus fails to teach efficient accessioning for a current test, let alone addressing the security problems associated with mass testing or gathering personally identifiable information.

None of the teachings of the above references, individually or in combination, facilitate accurate mass testing with the efficiency and security practically necessary for public acceptance to facilitate prevention, detection, or control of the spread of communicable diseases.

For these reasons, there is a need for facilitating mass testing with efficient accessioning of biological specimens to be tested. There is also a need for facilitating proactive notification of results of such tests to patients without requiring action from the patients to obtain the test results. There is a further need for facilitating accuracy of such accessioning and providing of the test results. There is also a need for facilitating security of personally identifiable information throughout such testing.

SUMMARY OF THE INVENTION

It is therefore an object of the present invention to provide methods and systems that facilitate secure and efficient mass testing by laboratories.

It is also an object of the present invention to provide methods and systems that achieve the above object and that also facilitate efficient accessioning of biological specimens to be tested.

It is another object of the present invention to provide methods and systems that achieve the above objects and that also facilitate proactively notifying patients with results of tests without requiring action from the patients after performing such tests as a prerequisite to obtain such results.

It is a further object of the present invention to provide methods and systems that achieve the above objects and that also facilitate increasing accuracy of accessioning biological specimens to be tested and of provision of results of such tests.

It is yet another object of the present invention to provide methods and systems that achieve the above objects and that facilitate increasing security of personally identifiable information throughout testing of biological specimens.

The invention achieves the above objects, as well as other objects and advantages that will become apparent from the description that follows, by facilitating securely and efficiently providing medical-test results. In some embodiments, first personally identifiable information is received for a first patient with a first biological specimen collected from the first patient. In some embodiments, the first biological specimen is received in a first container that bears a first container identifier. In some embodiments, the first personally identifiable information for the first patient and a first linking identifier (for example, an accession identifier used to track the first specimen during evaluation thereof, which in some embodiments, includes the first container identifier) are both stored in a first record of a first database. In some embodiments, the first biological specimen is evaluated to generate genetic values representative of the first biological specimen (or a biometric characteristic thereof). In some embodiments, the generated genetic values and the first linking identifier are stored in a first record of a second database. In some embodiments, the first biological specimen is also evaluated to generate a result of a first medical test or diagnosis. In some embodiments, the first biological specimen is tracked during the first medical test or diagnosis process using the first linking identifier. In some embodiments, the result of the first medical test is transmitted based on the first personally identifiable information for the first patient.

In some embodiments, after storing linking identifiers for patients in the first database, each container used to collect biological specimens from such patients is devoid of the linking identifier and does not have personally identifying information affixed thereto.

In some embodiments, a second biological specimen is collected from the first patient after the first biological specimen. In some embodiments, after receiving the first biological specimen, the second biological specimen is received in a second container that bears a second container identifier and without personally identifiable information for the first patient. In some embodiments, the second container does not bear the first linking identifier or the first container identifier and does not have affixed thereon personally identifiable information of the first patient. In some embodiments, the second biological specimen is evaluated to generate values representative of the second biological specimen (or biometric characteristics thereof such as a genetic sequence or genetic fingerprint). In some embodiments, a portion of the values generated for the second biological specimen are matched with a portion of the values generated for the first biological specimen as stored in the first record of the second database. In some embodiments, the first linking identifier is obtained from the first record of the second database based on matching the portion of the values generated for the second biological specimen with the portion of the values generated for the first biological specimen in the first record of the second database.

In some embodiments, the second biological specimen is evaluated to generate a result of a second medical test. In some embodiments, the second biological specimen is tracked during the second medical test based on the second container identifier. In some embodiments, the result of the second medical test is linked with the first personally identifiable information in the first record of the first database based on a match between the first linking identifier obtained from the first record of the second database with the first linking identifier in the first record of the first database. In some embodiments, the result of the second medical test is transmitted to the patient based on the first personally identifiable information obtained based on the link. Accordingly, the first linking identifier facilitates increasing security by enabling storage of the first personally identifiable information separate from the values generated for the first biological specimen and facilitates providing the result of the second medical test to the first patient without the first patient providing personally identifiable information with the second biological sample.

In some embodiments, the first database is stored on a first computing system and requires first credentials to access the first record of the first database, and the second database is stored on a second, different computing system and requires second credentials to access the first record of the second database. In some embodiments, the first record of the first database is not accessible with the second credentials, and the first record of the second database is not accessible with the first credentials. In some embodiments, the first and second computing systems are isolated from each other. In some embodiments, the first database is housed at a first geographic location, and the second database is housed at a second geographic location that is separate and distinct from the first geographic location.

In some embodiments, the values generated for the first biological specimen and the values generated for the second biological specimen provide a DNA fingerprint.

In some embodiments, the result of the second medical test includes the first personally identifiable information obtained based on the link.

In some embodiments, based on evaluation of a third biological specimen collected from a second patient, values generated that represent the third biological specimen (or biometric characteristics thereof) are used to determine that at least a portion of such generated values match at least a portion of the values generated for the first biological specimen collected from the first patient. In some embodiments, an alert is generated based on such match.

BRIEF DESCRIPTION OF THE DRAWINGS

Preferred embodiments of the present invention are described in detail below with reference to the following drawings.

DETAILED DESCRIPTION OF THE PREFERRED EMBODIMENT

Figure 1:
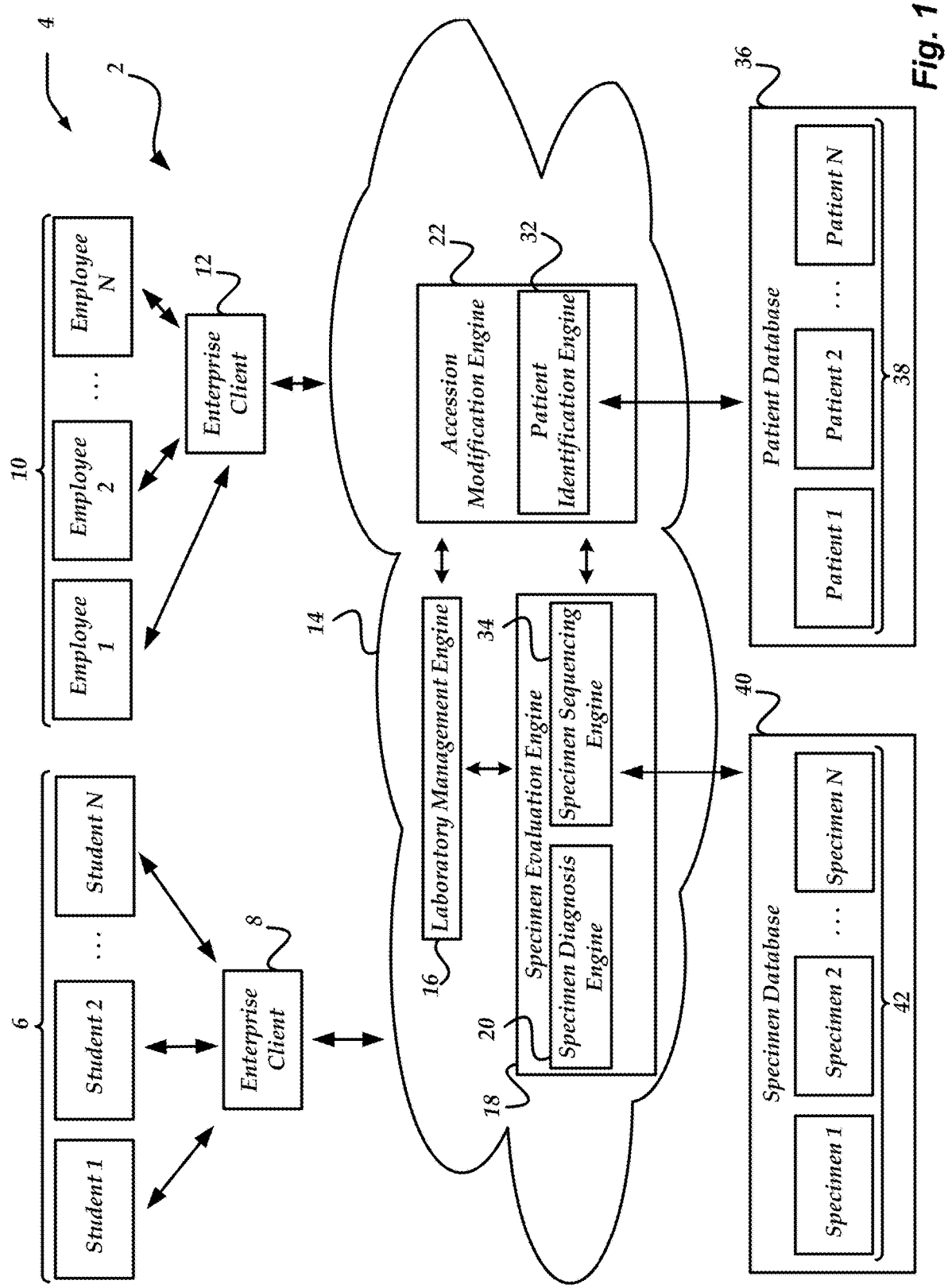
FIG. 1 shows a schematic representation of a laboratory diagnosis and reporting system according to principals of the invention.

A laboratory diagnosis and reporting system in accordance with the principles of the invention is generally indicated at reference number 2 in the Figures of the attached drawings, wherein numbered elements in the Figures correspond to like numbered elements herein.

Embodiments described herein provide methods, devices, and systems for laboratory diagnosis and reporting. In some embodiments, the laboratory diagnosis and reporting system 2 securely and efficiently provides laboratory diagnosis and reporting of such diagnosis based on evaluation of biological specimens. The system 2 enables efficient mass testing by eliminating the requirement that patients provide personally identifying information after giving their first biological specimen to be tested. When a patient gives their first specimen, the patient provides personal information to facilitate notifying the patient or guardian of the diagnosis based on evaluation of the first specimen. This personal information is recorded and used to deliver future test results to the patient or guardian based on evaluation of future biological specimens without requiring the patient to provide personal information with such future specimens. During the initial test for the patient, values representative of the patient's first specimen are also recorded. In some embodiments, such values include or represent deoxyribonucleic acid (DNA) sequences or other biological markers that provide substantially unique identifiers. When the patient gives a subsequent specimen, the system 2 facilitates the patient giving only the specimen, without any personal information. The system 2 is configured to evaluate the subsequent specimen to look up the patient's personal information by using values representative of the patient's subsequent specimen.

In some embodiments, the system 2 and associated processes facilitate privacy and security by separately storing biometric identifiers and personal data. In some embodiments, DNA identifiers and personal data are stored in separate databases, housed on separate computing systems at separate datacenters or isolated networks, require different credentials for respective access thereto, or are otherwise isolated from each other. In some embodiments, the records in these databases are linked or associated by way of a linking identifier or key. Some embodiments define the linking identifier as or based on an identifier affixed to the container (e.g., tube, vial, or others) used to collect the first specimen (e.g., a unique container identifier), which in some embodiments, includes a number or alphanumeric string encoded in a machine-readable format such as a serial number, a barcode, a quick response (QR) code engraved, embedded in, printed on, or otherwise affixed to the container, such as with an element affixed thereto bearing the container identifier such as a label or a radio frequency identification (RFID) tag. Such definition of the linking identifier promotes efficiency compared to independently generating a unique linking identifier by reducing the computational load on the system 2 and enabling auditing of the entire process throughout the system, while facilitating the diagnostic evaluation of the first specimen using the same linking identifier to track the container and thus the first specimen throughout the laboratory diagnostic process, thereby reducing a likelihood of errors. In some embodiments, the system 2 retrieves personal data by first performing a lookup to retrieve the linking identifier based on the biometric identifier, followed by a second lookup to retrieve the personal data based on the linking identifier.

FIG. 1 is a functional block diagram that illustrates the laboratory diagnosis and reporting system 2 according to some embodiments. The system 2 is shown in a mass-testing environment 4. The testing environment 4 includes the laboratory diagnosis and reporting system 2, a first enterprise 6 (e.g., a school or daycare) with students that are regularly tested for communicable disease, an enterprise client 8 that serves as a point of contact with respect to the laboratory diagnosis reports for the students of the first enterprise 6, a second enterprise 10 (e.g., an airport) with employees that are regularly tested for communicable disease, and an enterprise client 12 that serves as a point of contact for the laboratory diagnosis reports for the employees of the second enterprise 10. In some embodiments, the system 2 includes various engines implemented in a cloud-computing environment 14.

Figure 2:
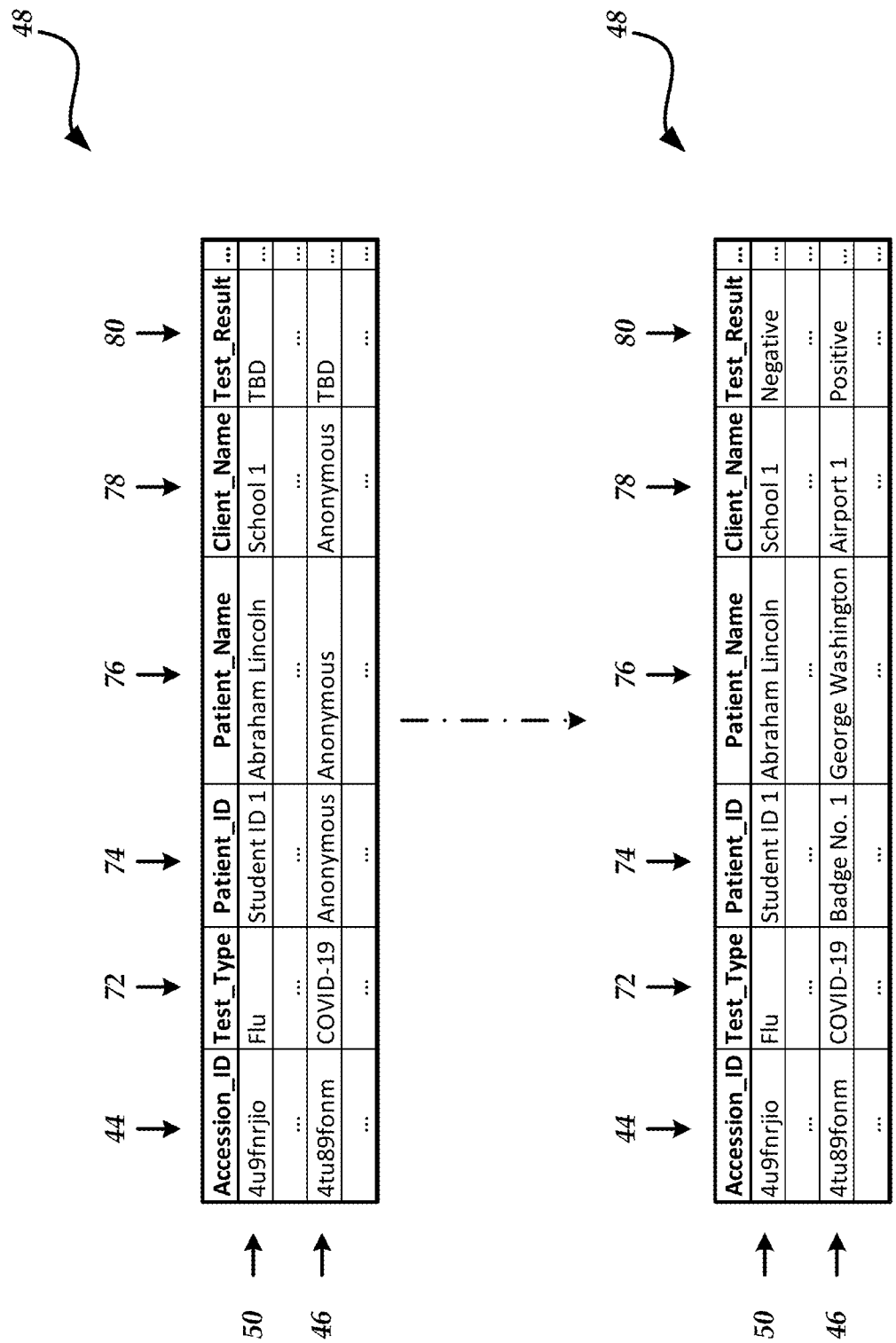
FIG. 2 illustrates a schematic representation of original and modified accession information before and after a diagnosis and accession-modification process performed by the system of FIG. 1.

As shown in FIG. 1, the system 2 includes a laboratory management engine 16 that, in some embodiments, facilitates accessioning biological specimens for laboratory diagnosis, tracking the diagnosis process, and generating and transmitting reports of the laboratory diagnosis to the enterprise clients 8, 12, which then optionally disseminate the diagnosis reports to the appropriate patients who are constituents of the respective enterprises 6, 10, as identified by the accession information after the diagnostic process (see FIG. 2). In some embodiments, the Bamert Regan enterprise clients 8, 12 are configured to collect biological specimens from the patients who are constituents of the enterprises 6, 10 and provide those collected biological specimens for accession. In some embodiments, such enterprise clients 8, 12 are configured to receive in bulk large quantities of containers in which biological specimens are collected, which occurs randomly, on a periodic basis such as the start of each week or shift change, or upon occurrence of an event such as a threshold number of constituents failing to attend for a period or shift. Accordingly, in some embodiments, the enterprise clients 8, 12 form part of the system 2.

As shown in FIG. 1, the system 2 includes a specimen evaluation engine 18, which includes a specimen diagnosis engine 20 that, based on evaluation of each collected specimen, performs a medical test to provide a medical test result or diagnosis and updates the management-engine information to include the result of the medical test (see FIG. 2). In some embodiments, the evaluation engine 18 or the diagnosis engine 20 receives the containers holding the respective biological specimens and tracks the containers and thus the specimens throughout the diagnostic process using the container identifiers (e.g., the accession identifier) affixed to such containers. In some embodiments, the diagnosis engine 20 provides the medical diagnoses for the respective specimens to the laboratory management engine 16 in connection with the respective container identifiers to facilitate the management engine 16 reporting such diagnostic results to the appropriate one of the enterprise clients 8, 12 (see FIG. 2). Accordingly, the evaluation engine 18 in some embodiments does not receive personal identifying information associated with the containers or the specimens.

As shown in FIG. 1, the system 2 includes an accession modification engine 22 that, in some embodiments, facilitates modifying the accession information generated by the laboratory management engine 16 for anonymously provided specimens for which the management engine 16 initially lacks personal information linking such specimens to patients (see FIG. 2). In some embodiments, the accession modification engine 22 generates the medical-test or diagnosis result report or transmits such report to the appropriate one of the enterprise clients 8, 12 or to the patients whose specimen is the basis of such report. In some embodiments, the accession modification engine 22 has a patient identification engine 32, and the specimen evaluation engine 18 has a specimen sequencing engine 34. The patient identification engine 32, in some embodiments, has exclusive access to a patient database 36 that includes records 38 that respectively store personal information for respective patients, along with a linking identifier unique to each respective patient but that, in some embodiments, fails on its own to enable identification of a patient. The specimen sequencing engine 34, in some embodiments, has exclusive access to a specimen database 40 that includes records 42 that respectively store values representative of biological specimens (e.g., DNA fingerprints or other biometrics), along with the linking identifier. This arrangement facilitates security while enabling the accession modification engine 22 to modify accession information generated by the laboratory management engine 16 for anonymously provided specimens.

In some embodiments, when the specimen evaluation engine 18 is provided with an anonymous biological specimen of a previously enrolled patient, the sequencing engine 34 generates values representative thereof (e.g., DNA fingerprints or other biometrics) and obtains the linking identifier from the specimen database 40 by determining which of the records 42 in the specimen database 40 stores a matching value representative of a biological specimen. In some embodiments, the patient identification engine 32 uses the obtained linking identifier to obtain personal information for the patient who provided the anonymous biological specimen by determining which of the records 38 in the patient database 36 stores a value matching the obtained linking identifier (see FIG. 3). In some embodiments, the sequencing engine 34 adds records to the specimen database 40 for new patients, and the patient identification engine adds records to the patient database 36 for new patients (see FIG. 3). In some embodiments, based on the obtained personal information, the accession modification engine 22 modifies the anonymous accession information of the laboratory management engine 16 to include the obtained personal information (see FIG. 2), thereby facilitating the provision of the medical diagnosis report to the patient without the patient providing personal information with the tested specimen for tests subsequent to the patient's first test.

In some embodiments, the specimen sequencing engine 34 is separate from and the specimen evaluation engine 18, such as in environments where different facilities conduct the diagnostic test than the facilities that conduct the specimen biometric analysis, in which case the specimen is typically divided up and shared by the separate facilities to permit running the respective evaluations in parallel rather than in serial. In some embodiments, the specimen sequencing evaluation engine 34 evaluates specimens to generate values representative of such specimens (e.g., DNA fingerprints), and in other embodiments, the specimen sequencing evaluation engine 34 obtains such values based on evaluation by another engine in the system 2, such as the specimen diagnosis engine 20 or the specimen evaluation engine 18. In either case, the specimen sequencing engine 34 evaluates, in some embodiments, only the specimens or values representative thereof and not personal information of patients (see the right side of FIG. 3). The specimen sequencing engine 34, in some embodiments, employs the unique container identifier or another accession identifier as the linking identifier and provides it to the patient identification engine 32 without the specimen or values representative of such specimen. Accordingly, in some embodiments, the patient identification engine 32 evaluates only the personal information and linking identifiers and not specimens or values representative thereof (see the left side of FIG. 3). The accession modification engine 22 therefore, in combination with such exclusive access to the respective patient and specimen databases 36, 40, facilitates secure and efficient laboratory diagnosis and reporting of such diagnostic test results without patients providing personal information with specimens to be evaluated subsequent to initial enrollment.

FIG. 1 depicts an illustrative bulk-testing scenario in which a large number of patients give biological specimens, those specimens are tested for a particular marker, condition, or disease, and the corresponding test results are reported. Some of the patients are new patients, meaning that they have not yet been tested in the illustrated environment 4. Student 1 is a new patient. Other patients such as Employee 1 are return patients, meaning they have previously given a biological specimen for testing. Accordingly, the system 2 facilitates Employee 1 to submit only a biological specimen without personally identifying information such as name, address, identity numbers, medical record numbers, employer identification, or others. New patients (e.g., Student 1) are asked to provide a specimen along with personally identifying information, such as name, address, identity numbers, or others to facilitate future diagnosis with submission of only a biological specimen on which such diagnosis is performed.

In the embodiment of FIG. 1, biological specimens and, for new patients only, personal information are provided to the enterprise clients 8, 12. Biological specimens are typically collected and provided in a container, such as a test tube. The container is marked with an identifier that is in some embodiments encoded on a label in a machine-readable format, such as by a barcode. In the illustrative scenario of FIG. 1, return patient Employee 1 provides a biological specimen in a container that is marked with the container identifier shown in FIG. 2 as the value of attribute 44 for record 46, which represents the accession information for the anonymous currently evaluated specimen collected from Employee 1, which defines a portion of the bulk accession file 48 created and maintained by the laboratory management engine 16 to facilitate tracking and managing the diagnostic and reporting process. In some embodiments, the laboratory management engine 16 defines the accession identifier as the container identifier, as shown in FIG. 2. New patient Student 1 provides a specimen in a container that is marked with the container identifier shown in FIG. 2 as the value of attribute 44 for record 50.

The enterprise clients 8, 12 uses provides the received information including patient information (for new patients) and container identifiers, along with the collected specimens in their respective containers for the laboratory accessioning and diagnosis. In some embodiments, the enterprise clients 8, 12 include depository devices configured to receive collected specimens and optionally patient information directly from patients. In some embodiments, the depository devices receive a sealed specimen, and in other embodiments, the depository devices receive an unsealed specimen and seal it into a container.

If a patient is a new patient, the patient's information is stored into the system 2 during intake or enrollment. The patient information is in the embodiment shown in FIG. 1 stored in a patient information database 36. In some embodiments, the database 36 associates a unique link identifier (LID) with each patient record (see attribute 62 in database 36 of FIG. 3). As discussed further below, such linking identifier links the patient record with another record stored in a separate database, as represented by the line 64 in FIG. 3 that schematically illustrates isolation between the databases 36, 40 (compare the values of attribute 62 in database 36 in FIG. 3 with the values of attribute 66 in database 40 in FIG. 3). The linking identifier in the illustrated embodiment is the container identifier of the container used by a patient to give an initial specimen (compare the value of attribute 44 of record 50 for the newly onboarded patient in FIG. 2 with the value of attribute 62 for record 68 in database 36 in FIG. 3 and with the value of attribute 66 for record 70 in database 40 in FIG. 3). In some embodiments, the patient database 36 may also associate medical record numbers or other generated identifiers with patient records such as contact information for where or to whom to send diagnostic reports (see FIG. 3).

When the enterprise client 8 or 12 completes the intake of specimens and patient information, it instructs the system 2 to produce a test list (e.g., bulk accession file 48 in FIG. 2). The test list is a list of container identifiers along with optionally collected personal information for some patients (e.g., new patients). In some embodiments, the test list contains as few as one initially populated attribute, such as the container identifier (see the values of attribute 44 in FIG. 2), which is in some embodiments the value represented by a barcode on each container for the specimen provided by return patients such as Employee 1. In some embodiments, a second initially populated attribute in the test list optionally identifies the type of medical test that should be performed for the collected specimen (see the values of attribute 72 in FIG. 2), even for return patients because enterprises in some embodiments are permitted to select fewer than all possible diagnostic tests or to rotate selection of diagnostic tests on a schedule or at random. In some embodiments, for new patients such as Student 1, more attributes are populated with personal information such as an identifier used by the patient's enterprise to internally identify the patient (e.g., a badge number or a student identification number) as shown by attribute 74 in FIG. 2, a name of the patient as shown by attribute 76 in FIG. 2, or an identification of the enterprise of which the patient is a constituent as shown by attribute 78 in FIG. 2.

In some embodiments, the test list is generated by the laboratory management engine 16 as accession information in the accession file 48 (see FIG. 2). In some embodiments, the laboratory management engine is executed by or includes a laboratory information system (LIS) to perform the processes described herein with respect to the laboratory management engine 16. In some embodiments, the laboratory management engine 16 provides (e.g., transmits, sends, or makes accessible) the test list to specimen diagnosis engine 20. In some embodiments, the diagnosis engine 20 uses or includes one or more diagnostic devices to evaluate the provided specimens to conduct medical diagnostic tests (e.g., polymerase chain reaction testing devices) and, in some embodiments, performs such tests in bulk (e.g., for example, mixing portions of specimens to conduct a single test for a group of patients and performing further tests on portions of specimens if the mixture generates a positive test result to identify a subgroup of specimens or individual specimens that triggered the positive test result). For each specimen, the diagnosis engine 20 produces a test result, such as an indicator that denotes whether a particular specimen tested positive for a particular condition, disease, or other evaluated characteristic.

In some embodiments, the diagnosis engine 20 produces a result set for numerous specimens at once in bulk, and in some embodiments, such information is used to supplement the accession information of the laboratory management engine 16 as shown in FIG. 2. In some embodiments, the result set is a list of records, each of which includes a container identifier (see the values of attribute 44 in the bottom of FIG. 2), optionally a specimen identifier (i.e., the value representative of the biometric characteristic of the specimen) (provided to the specimen sequencing engine 34 in some embodiments), and a test result (see the values of attribute 80 in the bottom of FIG. 2).

In some embodiments, the specimen evaluation engine 18 or the specimen sequencing engine 34 uses or includes one or more biometric analysis devices, such as a device that facilitates genetic sequencing (e.g., a mass array system as provided by Agena® Bioscience), to evaluate a biometric characteristic of the specimen that substantially uniquely identifies the patient, such as a partial genetic sequence or fingerprint, to generate a value that represents such biometric characteristic of the specimen. In either embodiment, the system 2 generates the value representative of the specimen (i.e., the value representative of a substantially unique biometric characteristic of the specimen) for each specimen evaluated for the medical diagnostic test. In some embodiments, the specimen sequencing engine 34 queries the specimen database 40 for at least a partial match or a best match above a predetermined threshold to determine which record 42 in the specimen database 40 stores values representative of a previously collected specimen (i.e., the value representative of a substantially unique biometric characteristic of the previously collected specimen). In some embodiments, the sequencing engine 34 determines that a match is found and obtains the linking identifier in the record that stores the matching value (see the value of attribute 66 for record 92 in database 40 in FIG. 3). In some embodiments, if no such match is found in the specimen database 40, the sequencing engine stores the value representative of the current specimen in a newly added record in the specimen database with the current accession identifier as the linking identifier, as shown by the specimen value attribute 94 and the linking identifier attribute 66 for the record 70 in the specimen database 40, which the sequencing engine 34 added for the new patient Student 1.

In some embodiments, responsive to the specimen sequencing engine 34 determining whether the specimen database 40 includes a match, the accession modification engine 22 handles the personal information for the patient. In some embodiments, if no specimen match was found, the patient identification engine 32 adds the accession identifier (e.g., the container identifier) as a linking identifier for a new record for the new patient such as Student 1 along with the personal information for the new patient (see the value of the linking identifier attribute 62, the patient identifier attribute 96, patient name attribute 98, and client name attribute 100 such as the enterprise name for the new record 68 for Student 1), which in some embodiments, is obtained from the accession file 48 in FIG. 2. Accordingly, the system 2 facilitates the new patient obtaining future test results on future specimens when such patient provides only the future specimens without personal information.

Figure 3:
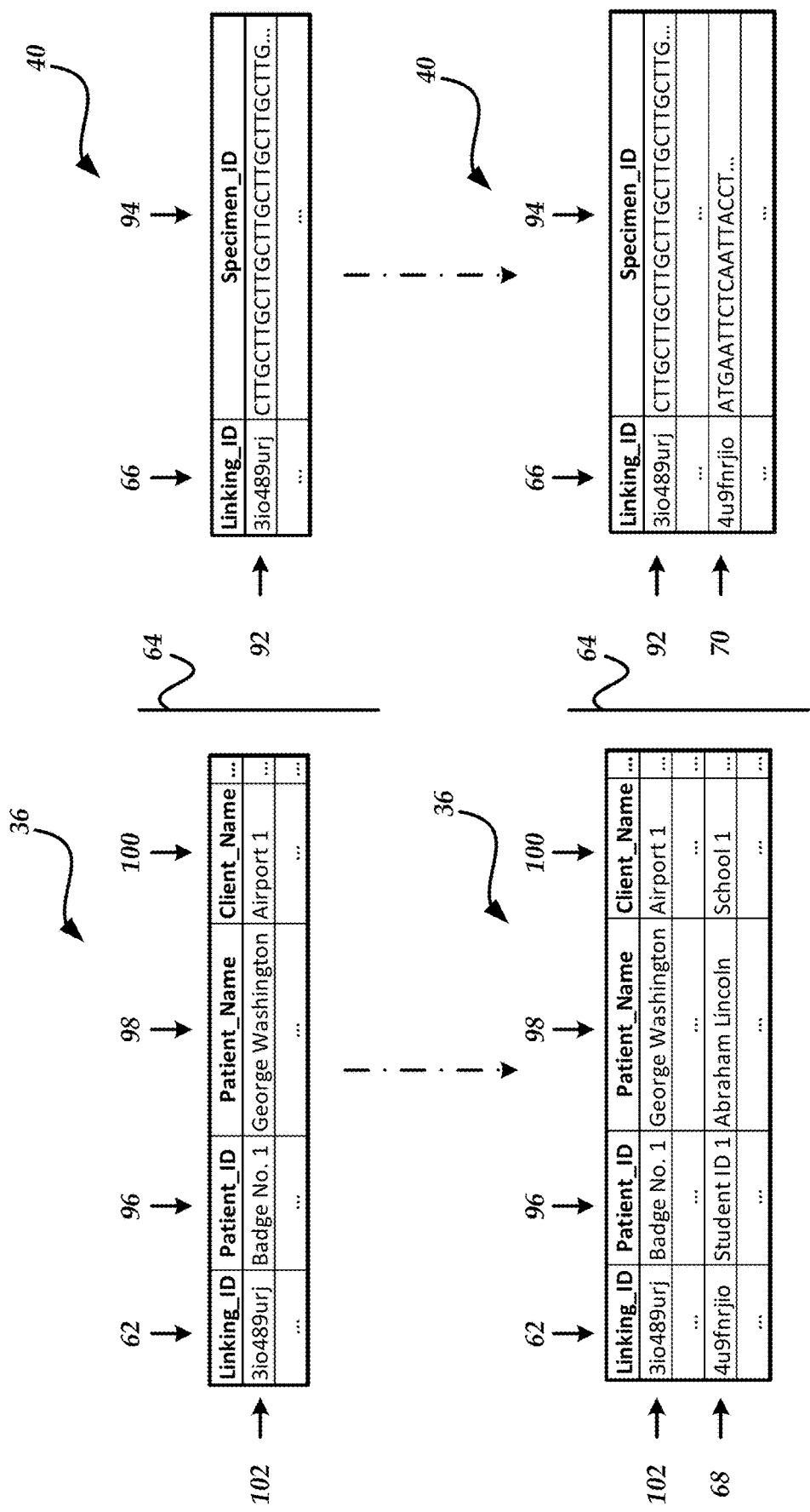
FIG. 3 shows a schematic representation of original and updated patient and specimen databases utilized and maintained by the system of FIG. 1.

In some embodiments, if a specimen match was found by the specimen sequencing engine 34, the patient identification engine 32 uses the linking identifier obtained by the sequencing engine 34 to lookup which of the records 38 in the patient database 36 includes the same linking identifier and obtains the personal information in such matching record (e.g., the matching value of the linking identifier attribute 62 for record 102 in the patient database 36 in FIG. 3). In some embodiments, the accession modification engine 22 updates the accession information in the accession file 48 in FIG. 2 to include the obtained personal information for the returning patient (see updated record 50 in the bottom of FIG. 2) to facilitate reporting the value of the test result for the anonymously provided specimen collected from such returning patient (see the value of the test result attribute 80 for record 50 in the bottom of FIG. 2). Accordingly, the specimen sequencing engine 34 and the accession modification engine cooperatively obtain patient information that is associated with information obtained in the result set for anonymously provided specimens and cooperatively create new associations between linking identifiers (e.g., accession or container identifiers, such as values encoded by barcodes on specimen-collection containers that uniquely identify such containers and thus specimens contained therein), specimen identifiers (e.g., DNA sequences or DNA fingerprints), and personal information for all new patients.

In some embodiments, the system 2 facilitates the specimen database 40 and the patient database 36 being stored on distinct computing or storage systems that are isolated from one another. By storing such data in a distributed or disaggregated manner, an additional layer of security is obtained, such that if a malicious party breaks into specimen database 40 they would only learn values that are unusable on their own, such as prior accession or container identifiers. In some embodiments, those values alone do not directly identify patients, and thus would be of little use to a malicious party. In some embodiments, the system 2 also facilitates isolating the patient database 36 from all data directly accessible through the specimen evaluation engine 18, such as the diagnostic data or results of the specimen diagnosis engine 20. In some embodiments, the computing or storage systems are logically isolated (e.g., via separate virtual private networks) or physically isolated (e.g., via separate networks, on separate computing systems, or in separate datacenters).

Notably, when bulk or mass testing at the enterprise level on a regular basis at scale, return patients are far more common than new patients, further reducing the exposure of personal information during the specimen collection and diagnostic process due to the system 2 facilitating anonymous specimen collection and evaluation for diagnosis. Moreover, such anonymous specimen collection and evaluation greatly increases efficiency due to the elimination of a requirement for the enterprise clients 8, 12 to collect personal information for such returning patients, which decreases the time per specimen collection and also decreases the likelihood of errors during the collection process.

In some embodiments, the specimen sequencing engine 34 is separate from the specimen evaluation engine 18. In some embodiments, the specimen evaluation engine 18 provides the value representative of the currently evaluated specimen to the accession modification engine 22 or the laboratory management engine 16, which provides such value to the specimen sequencing engine 34 to enable the sequencing engine 34 to query the specimen database 40 for a match. In some embodiments, a match between values representative of specimens is based on at least a partial match that exceeds a predetermined threshold indicative of a statistically acceptable level of certainty that the specimens were collected from the same individual (e.g., statistically no more than 1 in every 100,000 people are likely to have such match), such as matching a predetermined number of genetic markers or sequences. In some embodiments, the specimen sequencing engine 34 is separate from the patient identification engine 32 and each engine that includes the patient identification engine 32 such as the accession modification engine 22 to promote isolation between the patient identification engine 32 and the specimen sequencing engine 34 and thus further isolation between the patient database 36 and the specimen database 36.

In some embodiments, the specimen diagnosis engine 20 is separate from the specimen evaluation engine 18. In some embodiments, the specimen evaluation engine 18 provides characteristics or values of the current specimen to be diagnosed (e.g., ribonucleic acid (RNA) sequence values) to the accession modification engine 22 or the laboratory management engine 16, which provides such values to the specimen diagnosis engine 20 to enable the specimen diagnosis engine 20 to generate a medical-test or diagnosis result. In some embodiments, the accession modification engine 22 includes the specimen diagnosis engine 20. In some embodiments, responsive to the medical-test results from the diagnosis engine 20 and the accession-modification information from the accession modification engine 22, the laboratory management engine 16 creates a test report. In some embodiments, the respective test reports for the enterprises 6, 10 include respective lists of the test results for each patient whose specimen was evaluated for a medical test and who is a constituent of the respective enterprise 6 or 10, such as by associating a patient name with an indicator that their test was positive or negative. In another embodiment, multiple test reports are created for each enterprise 6 or 10, each individualized for one specific patient. In some embodiments, the reports for the patients associated with the enterprises 6, 10 are provided to the respective enterprise clients 8, 12 for evaluation and dissemination to the appropriate personnel in the enterprise 6, 10. In other embodiments, the reports are provided directly to the patients.

Figure 4:
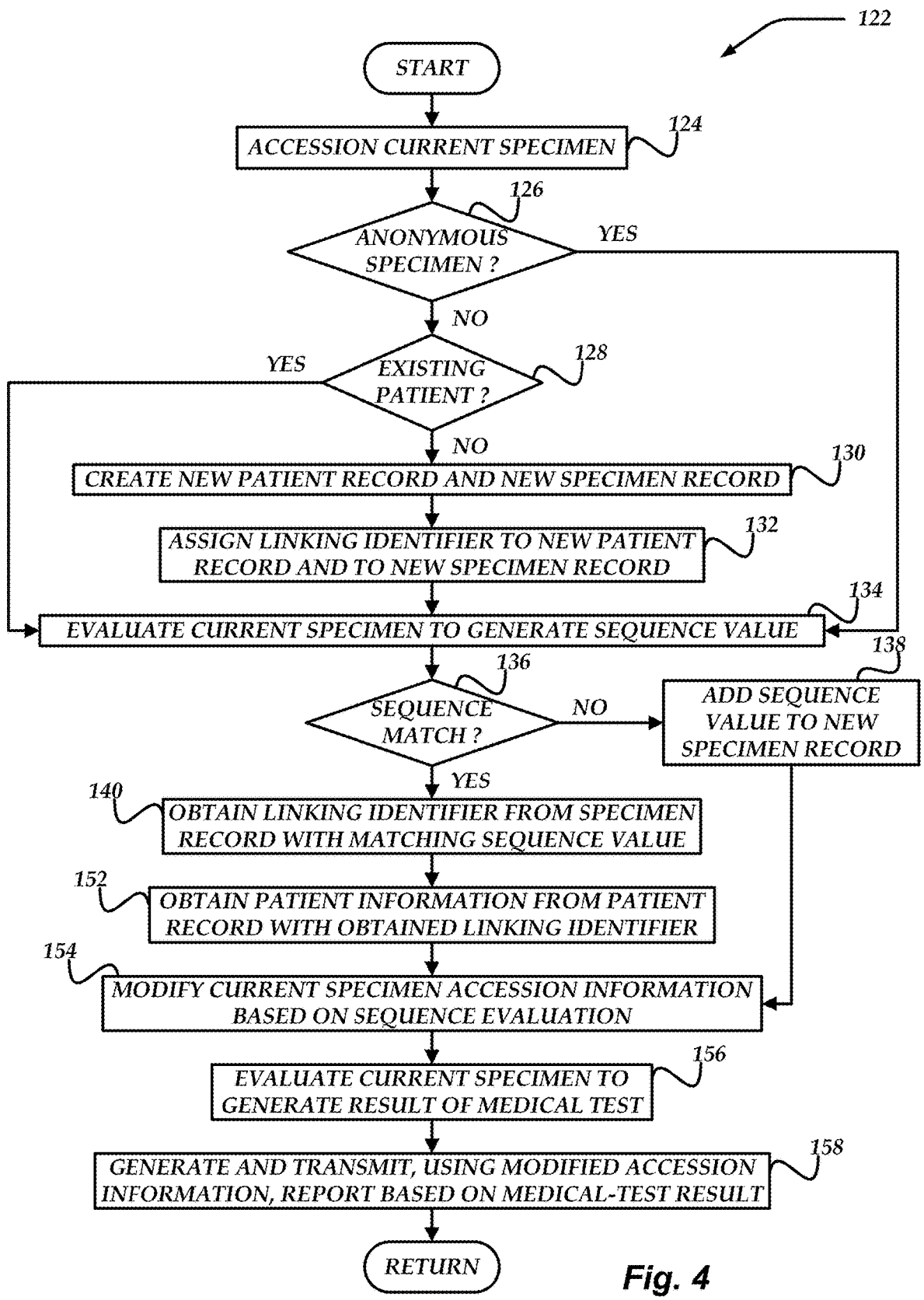
FIG. 4 illustrates an overview flowchart of a process for laboratory diagnosis and reporting for a currently evaluated specimen, executed by the system of FIG. 1.

FIG. 4 shows a logical overview flow diagram that illustrates a medical diagnosis and reporting process 122 implemented, performed, or executed by the system 2 according to some embodiments. In some embodiments, one or more elements of the system 2 implement, perform, or execute one or more portions of the process 122, as discussed above with respect to FIG. 1. In some embodiments, the process 122 initiates at a start block responsive to a patient or a set of patients submitting new biological specimens to an enterprise client of the enterprise of which the patients are constituents or responsive to the enterprise client submitting the new specimens to a laboratory for diagnosis. The process 122 is generally discussed with respect to a single new specimen for ease of understanding, yet the process 122 is executed in some embodiments with respect to a batch of current specimens at once or in parallel to facilitate mass testing at bulk scale on the enterprise level.

After the start block, in block 124, a new specimen is accessioned as a current specimen. In some embodiments, accessioning includes receiving a specimen, logging a specimen or container identifier into a laboratory information system (e.g., the laboratory management engine 16), creating system orders to trigger other components or engines in the system 2 to initiate other actions in the process 122, and for new patients, gathering associated personal information, such as a patient's name, address, employer, medical identification number, or others. The upper portion of FIG. 2 shows an embodiment of an accession file 28 that includes information generated during accession of several current specimens.

At decision block 126, the accession information generated for the current specimen at block 124 is evaluated to determine whether the specimen is anonymous (i.e., whether the current specimen was collected with personal information for the patient from whom the current specimen was collected), and if the specimen is anonymous, the process 122 proceeds to decision block 128; otherwise, the process 122 flows to block 134. An anonymous specimen is a specimen collected and received by the system 2 without personally identifying information for the patient from whom the specimen was collected. In some embodiments, a specimen is collected with information that identifies the enterprise of which the patient is a constituent and without personal information for the client that enables identifying the patient distinctly from all other individual constituents of the enterprise, and in such case, the current specimen is considered an anonymous specimen. As discussed above, anonymous specimens are typically collected when a patient is a return patient. In general, if the record in the current specimen in the accession file 48 lacks information distinct for the patient from whom the current specimen was collected (e.g., no values populated for the attributes 74 and 76 in the current specimen record) that enables uniquely identifying the patient from other patients identified in the patient database 36 in FIG. 1 or in the enterprise of which the patient is a constituent, it is determined that the current specimen is anonymous.

At block 128, the accession information generated for the current specimen at block 124 is evaluated to determine whether the patient is an existing patient, and if so, the process 122 proceeds to block 130; otherwise, the process 122 proceeds to block 134. In some embodiments, a patient is determined to be an existing patient responsive to information that the patient provided with the current specimen (e.g., the patient intends for the information that the patient previously provided be updated, such as changing enterprises, names, addresses, or others). In some embodiments, a patient is determined to be an existing patient responsive to finding one or more portions of the patient's personal information provided with the current specimen in the patient database 36 in FIG. 1.

At block 130, a new patient record is created in the patient database 36 in FIG. 1, and a new specimen record is created in the specimen database 40 in FIG. 1. In some embodiments, the personal information included in the accession information for the current specimen is added to the new patient record (see the values of the personal information attributes in the new-patient record 68 added to the patient database 36 at the bottom of FIG. 2).

At block 132, a linking identifier is added to the new patient record and the new specimen record created at block 130. In some embodiments, the linking identifier is unique in the patient database 36 and is unique in the specimen database 40. In some embodiments, the linking identifier is the accession identifier that uniquely identifies the current specimen in the accession file for which the accession information is created in block 124. In some embodiments, the accession identifier is utilized by the laboratory information system, laboratory management engine 16, specimen evaluation engine 18, or specimen diagnosis engine 20 to track the current specimen or the container that holds the current specimen throughout the diagnosis of the current specimen. In some embodiments, the accession identifier is based on, is, or includes an identifier that uniquely identifies the container that holds the current specimen or was used to collect the current specimen from the patient. In some embodiments, such container identifier is a value encoded in a machine-readable format affixed to the container, such as a barcode on a label adhered to the specimen container or engraved on the container.

At block 134, the current specimen is evaluated to generate a value representative of a biometric characteristic of the current specimen or biological material in the current specimen, such as a genetic sequence or genetic fingerprint.

At decision block 136, the value generated at block 134 is evaluated to determine whether a record in the specimen database 40 in FIG. 1 has a value that matches the value generated at block 134, and if so, the process 122 proceeds to block 140; otherwise, the process 122 proceeds to block 138. In some embodiments, a record is determined to include a matching value when the stored value and the generated value have at least a partial match that exceeds a predetermined threshold indicative of a statistically acceptable level of certainty that the specimens were collected from the same individual, such as matching a number or percent of genetic markers or sequences that matches or exceeds a threshold number or percent.

At block 138, after no matching specimen value is determined to exist in the specimen database 36 in FIG. 1, the value generated at block 134 is added to the new specimen record created at block 130, and the process proceeds to block 154.

At block 140, after a matching specimen value is determined to exist in a specimen record of the specimen database 40 at block 136, the linking identifier associated with the matched specimen value is obtained. In some embodiments, the linking identifier is obtained from such specimen record in which the matching specimen value is stored. In some embodiments, the obtained linking identifier was assigned to such specimen record when such specimen record was created upon initial enrollment of the patient with a previous specimen from which such matching specimen value was generated during a previous execution of the process 122.

At block 152, the linking identifier obtained at block 140 is used to query the patient database 36 to obtain patient information in a patient record of the patient database 36 that includes or is otherwise associated with the obtained linking identifier. Considering the returning patient Employee 1, the process at block 152 includes using the value of the attribute 66 for the record 92 in the specimen database 40 to obtain the personal information (e.g., the values of the attributes 96, 98, 100) in the record 102 of the patient database 36 based on the record 102 including the linking identifier as the value of the attribute 62.

At block 154, the current specimen accession information (e.g., the accession information in the record for the current specimen in the accession file 48) is replaced, supplemented, or otherwise modified or updated based on the evaluation of the current specimen with respect to matches in the specimen database 40 or matches with respect to the linking identifier in the patient database 36. In some embodiments, such modification includes adding the personal information obtained at block 152 to the accession information for the current specimen, as shown in the bottom of FIG. 2 with respect to the record 46 for the returning patient Employee 1. Other modifications are described regarding process 172 of FIG. 5.

At block 156, the current specimen is evaluated to generate a medical test result. In some embodiments, the medical test or diagnosis result generated at block 156 is based on the evaluation of the current specimen at block 134. In other embodiments, the evaluation at block 156 is separate and distinct from the evaluation block 134. In either case, the evaluation used to generate the medical test or diagnosis result is of the current specimen collected from the patient and accessioned at block 124.

At block 158, a report of the medical test or diagnosis result is generated or transmitted using the modified accession information to facilitate notifying the patient or enterprise of which the patient is a constituent of such result.

In some embodiments, the process 122 continues operating until one or more events occur, such as reporting the results for all of the current specimens in a batch. Next, in some embodiments, control returns to a calling process.

Figure 5:
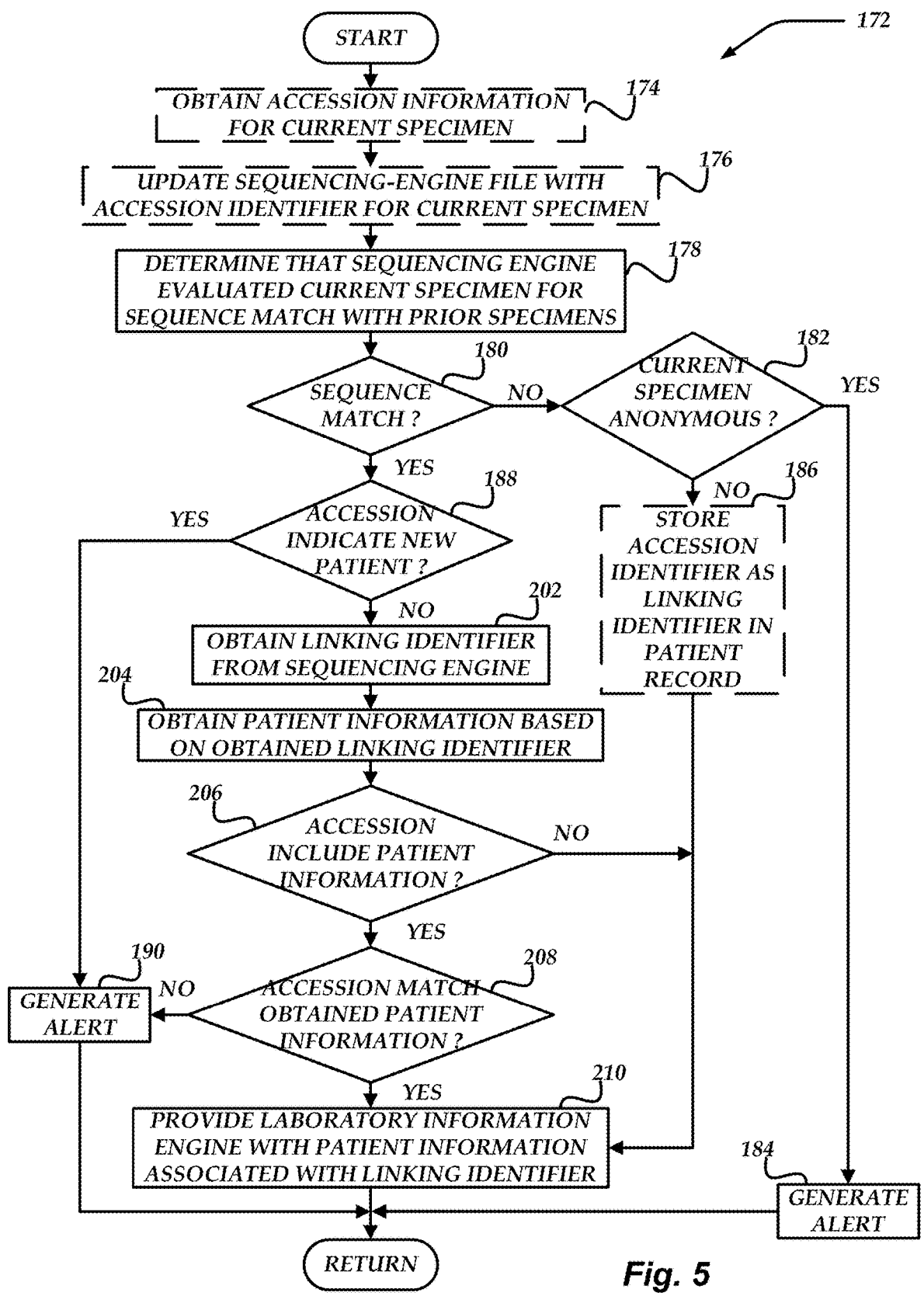
FIG. 5 shows a flowchart of a process for modifying accession information for a currently evaluated specimen, executed by an accession modification engine in the system of FIG. 1.

FIG. 5 illustrates a logical flow diagram of a process 172 for modifying accession information for a currently evaluated specimen implemented, performed, or executed by the system 2 according to some embodiments. The process 172 is described with respect to the same current specimen with respect to which the process 122 is described. In some embodiments, one or more elements of the system 2 (e.g., the accession modification engine 22 or the patent identification engine 32) implement, perform, or execute one or more portions of the process 172, as discussed above with respect to FIG. 1. In some embodiments, the process 172 initiates at a start block responsive to a system order that triggers the accession modification engine 22 to engage with the laboratory management engine 16 or the specimen evaluation engine 18. In some embodiments, generation of the accession file 48 or a record or another portion of such file 48 generates such trigger.

At block 174, accession information such as the accession identifier for the current specimen is obtained, such as from the accession record or file generated at block 124 in the process 122. At block 176, a file used by the specimen evaluation engine 18 or the specimen sequencing engine 34 (e.g., a sequencing-engine file) such as a comma-separated values (CSV) file with the accession identifier obtained at block 174. Blocks 174 and 176 facilitate the specimen evaluation engine 18 proceeding with their respective tasks in the process 122. However, blocks 174 and 176 are optional because, in some embodiments, the specimen evaluation engine 18 or its components obtain the accession identifier directly from the laboratory management engine 16 or the accession records or accession files (e.g., the accession file 48) generated at block 124 in the process 122.

At block 178, it is determined that the specimen sequencing engine 34 determined whether the specimen database 40 has a record that includes values that match the values representative of the current specimen generated in block 134 in the process 122. In some embodiments, the process 172 pauses at block 178 until such determination is made. In some embodiments, such determination provides the trigger for the start block of process 172.

At decision block 180, it is determined whether the evaluation of the current specimen resulted in finding a match in the specimen database 40 in FIG. 1 (i.e., whether the outcome of the decision block 136 was positive or negative in process 122 for the current specimen), and if not, the process 172 proceeds to decision block 182; otherwise, the process 172 proceeds to the decision block 188. In some embodiments, the determination of block 180 is based on evaluation of a value in the sequencing-engine file, and such value is provided by the specimen evaluation engine 18 or the specimen sequencing engine 34 and indicates the outcome of the decision block 136 in the process 122 for the current specimen.

At decision block 182, it is determined whether the current specimen is an anonymous specimen, and if so, the process 172 proceeds to block 184; otherwise, the process 172 proceeds to block 186. In some embodiments, the determination at block 182 is based on evaluation of the accession information as discussed with respect to block 126 of the process 122.

At block 184, an alert is generated because the specimen is anonymous and no match for the current specimen was found in the specimen database 40 in FIG. 1. In some embodiments, the alert is provided to the enterprise identified during the specimen accession as the enterprise from which the specimen was received to instruct the enterprise to have its constituents re-enroll or those new constituents to enroll. In some embodiments, the alert is provided to such enterprise only if the medical test or diagnosis report indicates that the specimen indicates a carrier of a disease. In some embodiments, the alert triggers the laboratory management engine 16 to transmit such instruction or the report to the enterprise.

At block 186, after it is determined that the current specimen is for a newly enrolling patient, a linking identifier is stored in the new patient record of the patient database 36 along with the personal information for the new patient. Optionally, the accession identifier is stored as the linking identifier.

At decision block 188, after it is determined that a match was found in the specimen database 40 in FIG. 1, it is determined whether the accession information for the current specimen indicates that the current specimen was collected from a new patient, and if so, the process 172 proceeds to block 190; otherwise, the process 172 proceeds to block 202. In some embodiments, the determination at block 188 is performed as described with respect to decision block 128 in the process 122.

At block 190, an alert is generated because the newly enrolling patient provided a biological specimen that produced a match based on a biological specimen previously provided by another patient (e.g., the new patient is a twin of the other patient). In some embodiments, the alert is provided to the new patient to instruct the new patient that the new patient must always provide at least some personal information to enable the system 2 to distinguish the new patient from the other patient. In some embodiments, the other patient is also instructed to always provide at least some personal information to enable the system 2 to distinguish the other patient from the new patient.

At block 202, after it is determined that a match has been found in the specimen database 40 of FIG. 1 for a returning patient, the linking identifier is obtained based on the specimen sequencing engine 34 obtaining such linking identifier from the specimen database 40. In some embodiments, the linking identifier is obtained from the sequencing-engine file responsive to the specimen evaluation engine 18 or the specimen sequencing engine 34 storing the linking identifier in such file in connection with the current specimen based on the match in the specimen database 40 for the current specimen.

At block 204, the obtained linking identifier for the current specimen is used to obtain the patient information for the current specimen from the record in the patient database 36 associated with the obtained linking identifier.

At decision block 206, it is determined whether the accession information for the current specimen includes patient information (e.g., whether the current specimen is an non-anonymous specimen for a returning patient or whether enterprise information was provided with the current specimen), and if so, the process 172 proceeds to decision block 208; otherwise, the process 172 proceeds to the block 210.

At decision block 208, after it has been determined that patient information was provided with the current specimen, it is determined whether the accessioned patient information matches the information in the patient database 36, and if so, the process 172 proceeds to block 210; otherwise, the process 172 proceeds to block 190. In some embodiments, the alert generated at block 190 after execution of decision block 208 is different, however, than the alert generated at block 190 after execution of decision block 188. In some embodiments, the alert generated at block 190 after execution of decision block 208 triggers manual intervention to reconcile the discrepancy between information collected from the patient or enterprise with the information in the patient database for such patient (e.g., manual evaluation of scanned documents containing the accession information previously collected with the original specimen from the patient and with the current specimen from the patient) because such discrepancy is possibly caused by illegible handwriting, typographical error, or others. In some embodiments, the generated alert at block 190 after execution of decision block 208 triggers the same action as the block 184.

At block 210, after it has been determined that the information in the patient database 36 matches the accessioned information, the accession information is replaced, supplemented, or otherwise updated or modified to include information obtained from the patient database 36. In some embodiments, the accession information is modified to include information related to or including one or more generated alerts described with respect to one or more of blocks 184, 190.

In some embodiments, the process 172 continues operating until one or more events occur, such as evaluating the sequencing-engine file for current specimens and determining whether the patient database 36 includes matches for each specimen for which the specimen database 40 produced a match until all of the current specimens in a batch are processed. Next, in some embodiments, control returns to a calling process.

Figure 6:
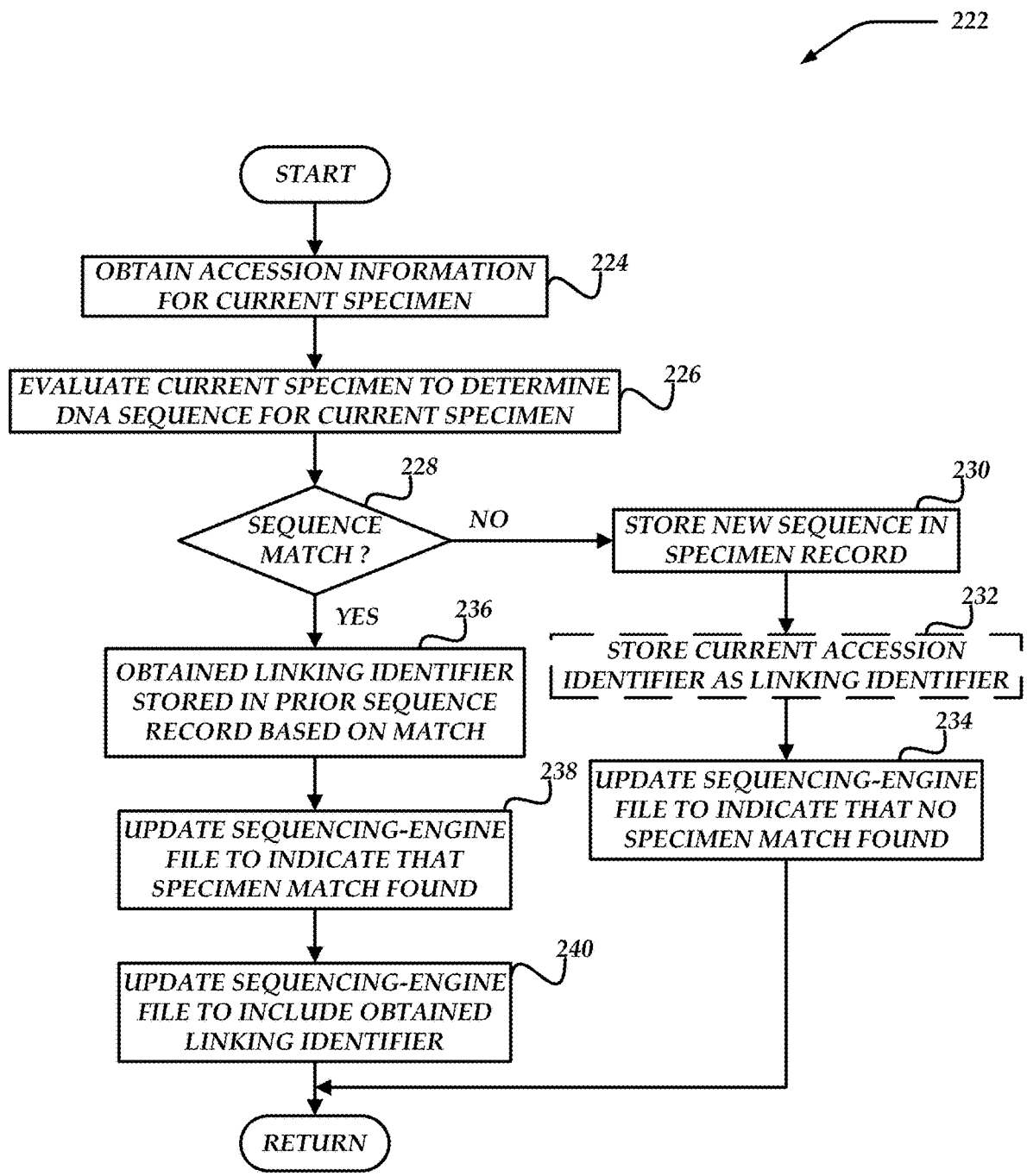
FIG. 6 illustrates a flowchart of a process for providing a linking identifier based on sequencing of a currently evaluated specimen, executed by a specimen sequencing engine in the system of FIG. 1.

FIG. 6 illustrates a logical flow diagram of a process 222 for providing a linking identifier based on evaluation of a current specimen implemented, performed, or executed by the system 2 according to some embodiments. The process 222 is described with respect to the same current specimen with respect to which the process 122 is described. In some embodiments, one or more elements of the system 2 (e.g., the specimen evaluation engine 18, the specimen diagnosis engine 20, or the specimen sequencing engine 34) implement, perform, or execute one or more portions of the process 222, as discussed above with respect to FIG. 1. In some embodiments, the process 222 initiates at a start block responsive to a system order that triggers the specimen evaluation engine 18 to evaluate the current specimen. In some embodiments, updating the sequencing-engine file as described with respect to block 176 of the process 172 generates such trigger.

At block 224, accession information such as the accession identifier for the current specimen is obtained, such as from the sequencing-engine file updated at block 176 of the process 172 or as described with respect to block 174 of the process 172. In some embodiments, the accession identifier for the current specimen is obtained directly from the laboratory management engine 16 or the accession records or accession files (e.g., the accession file 48) generated at block 124 in the process 122.

At block 226, the current specimen is evaluated to generate a value representative of a biometric characteristic of the current specimen or biological material in the current specimen, such as a genetic sequence or genetic fingerprint.

At decision block 228, it is determined whether the value generated at block 226 matches a value in a record in the specimen database 40, as described with respect to decision block 136 of the process 122, and if so, the process 222 proceeds to the block 230; otherwise, the process 222 proceeds to the block 236.

At block 230, after determining that the current specimen was collected from a new patient, a new record is created in the specimen database 40 of FIG. 1, and the value generated at block 226 is stored in the new record in the specimen database 40.

At block 232, a linking identifier is associated with the stored value generated at block 226, such as storing the linking identifier in the new record in the specimen database 40. Optionally, the linking identifier is based on, is, or includes the accession identifier for the current specimen.

At block 234, the accession modification engine 22 is notified that no specimen match was found in the specimen database with respect to the current specimen. In some embodiments, the sequencing-engine file is updated to indicate that no specimen match was found in the specimen database 40 with respect to the current specimen, as discussed with respect to block 178 or decision block 180 of the process 172 to facilitate the accession modification engine 22 proceeding accordingly.

At block 236, after finding a match in the specimen database 40 for the current specimen, a linking identifier is obtained from the specimen database 40 for the matching value in the specimen database 40. In some embodiments, the linking identifier is associated with the matching value in the specimen database 40, such as stored by the same record of the specimen database 40 as the matching value. In some embodiments, the linking identifier was previously stored as described with respect to the block 232 when the matching value was originally stored in the specimen database 40 as described with respect to the block 230 upon initial enrollment of the patient when a previous specimen was collected from such patient.

At block 238, the accession modification engine 22 is notified that a specimen match was found in the specimen database with respect to the current specimen. In some embodiments, the sequencing-engine file is updated to indicate that a match was found in the specimen database 40 match was found in the specimen database 40 with respect to the current specimen, as discussed with respect to block 178 or decision block 180 of the process 172 to facilitate the accession modification engine 22 proceeding accordingly.

At block 240, the accession modification engine 22 is provided with the linking identifier obtained from the specimen database 40 at block 236. In some embodiments, the sequencing-engine file is updated to include the obtained linking identifier as described with respect to block 202 of the process 172 to facilitate the accession modification engine 22 obtaining personal information from the patient database 36 for the patient from whom the current specimen was anonymously collected.

In some embodiments, the process 222 continues operating until one or more events occur, such as determining that all current specimens in a batch (e.g., those current specimens identified in the accession information of the accession file 48) have been evaluated for medical or diagnostic tests and for matches in the specimen database 40. Next, in some embodiments, control returns to a calling process.

Figure 7:
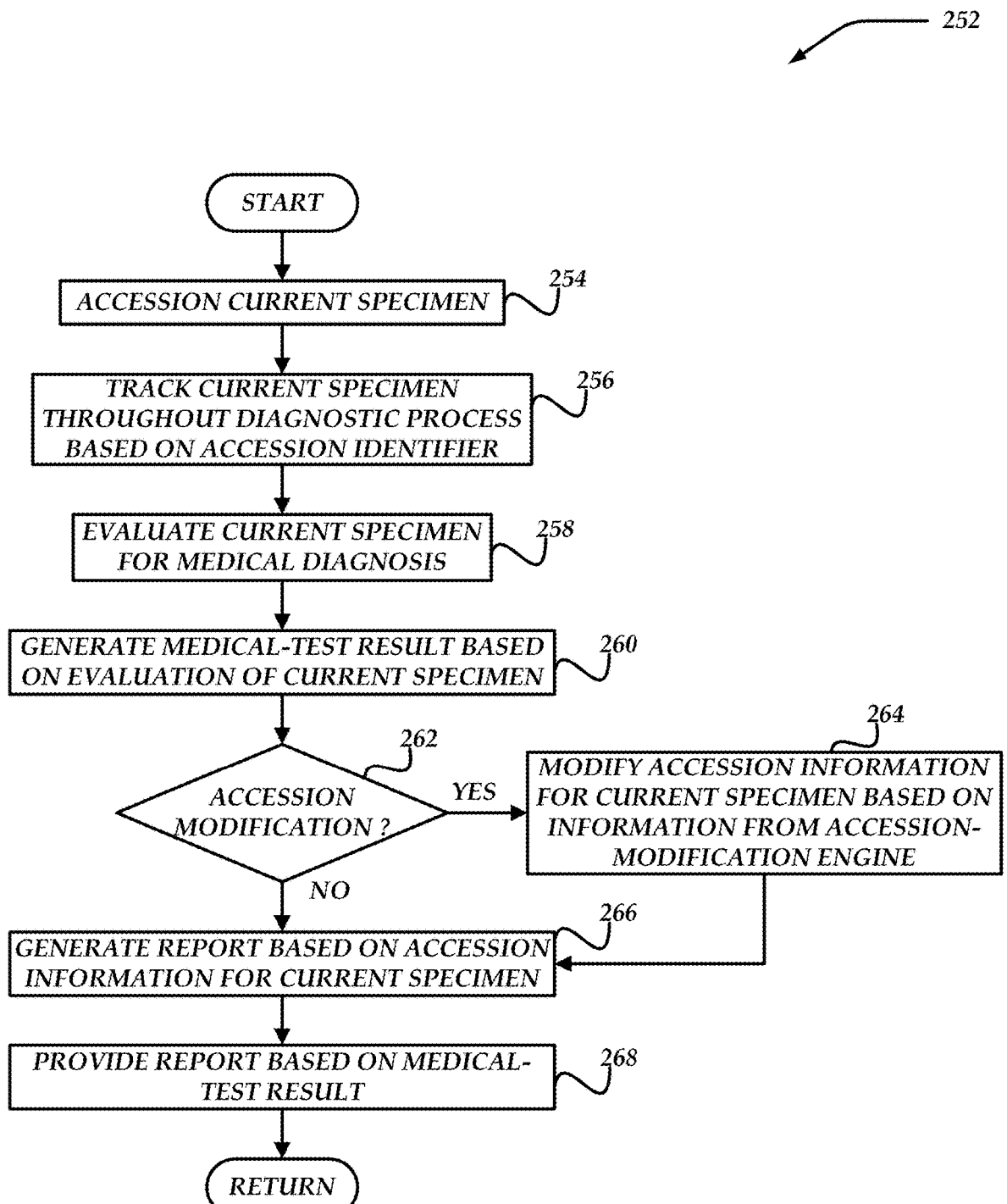
FIG. 7 shows a flowchart of a process for laboratory diagnosis and reporting for a currently evaluated specimen, executed by a laboratory management engine and specimen diagnosis engine in the system of FIG. 1.

FIG. 7 illustrates a logical flow diagram of a process 252 for laboratory diagnosis and reporting for a currently evaluated specimen implemented, performed, or executed by the system 2 according to some embodiments. The process 252 is described with respect to the same current specimen with respect to which the process 122 is described. In some embodiments, one or more elements of the system 2 (e.g., the laboratory management engine 16, the specimen evaluation engine 18, or the accession modification engine 22) implement, perform, or execute one or more portions of the process 252, as discussed above with respect to FIG. 1. In some embodiments, the process 252 initiates at a start block responsive to a system order that triggers the laboratory management engine 16 to accession the current specimen. In some embodiments, one or more of the enterprise clients 8, 12 providing a batch of collected specimens triggers the start of the process 252.

At block 254, the current specimen is accessioned, as discussed with respect to block 124 of the process 122.

At block 256, the current specimen is tracked throughout the testing or diagnostic process based on an accession identifier obtained when accessioning the current specimen at block 254. In some embodiments, the accession identifier is based on, is, or includes a container identifier that uniquely identifies the container in which the current specimen is collected or held.

At block 258, the current specimen is evaluated for medical diagnosis, such as in a medical test or diagnostic test, as discussed with respect to block 156 of the process 122.

At block 260, a medical-test result or diagnosis result is generated based on the evaluation of the current specimen at block 258, as discussed with respect to blocks 156 and 158 of the process 122.

At decision block 262, it is determined whether the accession information of block 254 should be replaced, supplemented, or otherwise updated or modified, as discussed with respect to one or more of blocks 184, 190, or 210 of the process 172, and if so, the process 252 proceeds to block 264; otherwise, the process 252 proceeds to the block 266. In some embodiments, a notification to make such modification is provided by the accession modification engine 22 of FIG. 1.

At block 264, after it is determined that the accession information for the current specimen should be updated, the accession information is replaced, supplemented, or otherwise modified or updated based on information provided by the accession modification engine 22, as discussed with respect to one or more of blocks 184, 190, or 210 of the process 172.

At block 266, the accession information (e.g., the modified accession information of block 264) is used to generate a report based on the medical-test or diagnostic test result for the current specimen, as discussed with respect to block 158 of the process 122.

At block 268, using the accession information (e.g., the modified accession information of block 264) the report of block 266 is provided to the appropriate enterprise client 8, 12, the appropriate enterprise 6, 10, or to the patient from whom the current specimen was collected, as discussed with respect to block 158 of the process 122. In some embodiments, one or more of blocks 266 or 268 are included in the process 172 executed by the accession modification engine 22 based on the medical-test or diagnosis result obtained from the specimen evaluation engine 18 or the laboratory management engine 16.

In some embodiments, the process 252 continues operating until one or more events occur, such as reporting the results for all of the current specimens in a batch. Next, in some embodiments, control returns to a calling process.

Figure 8:
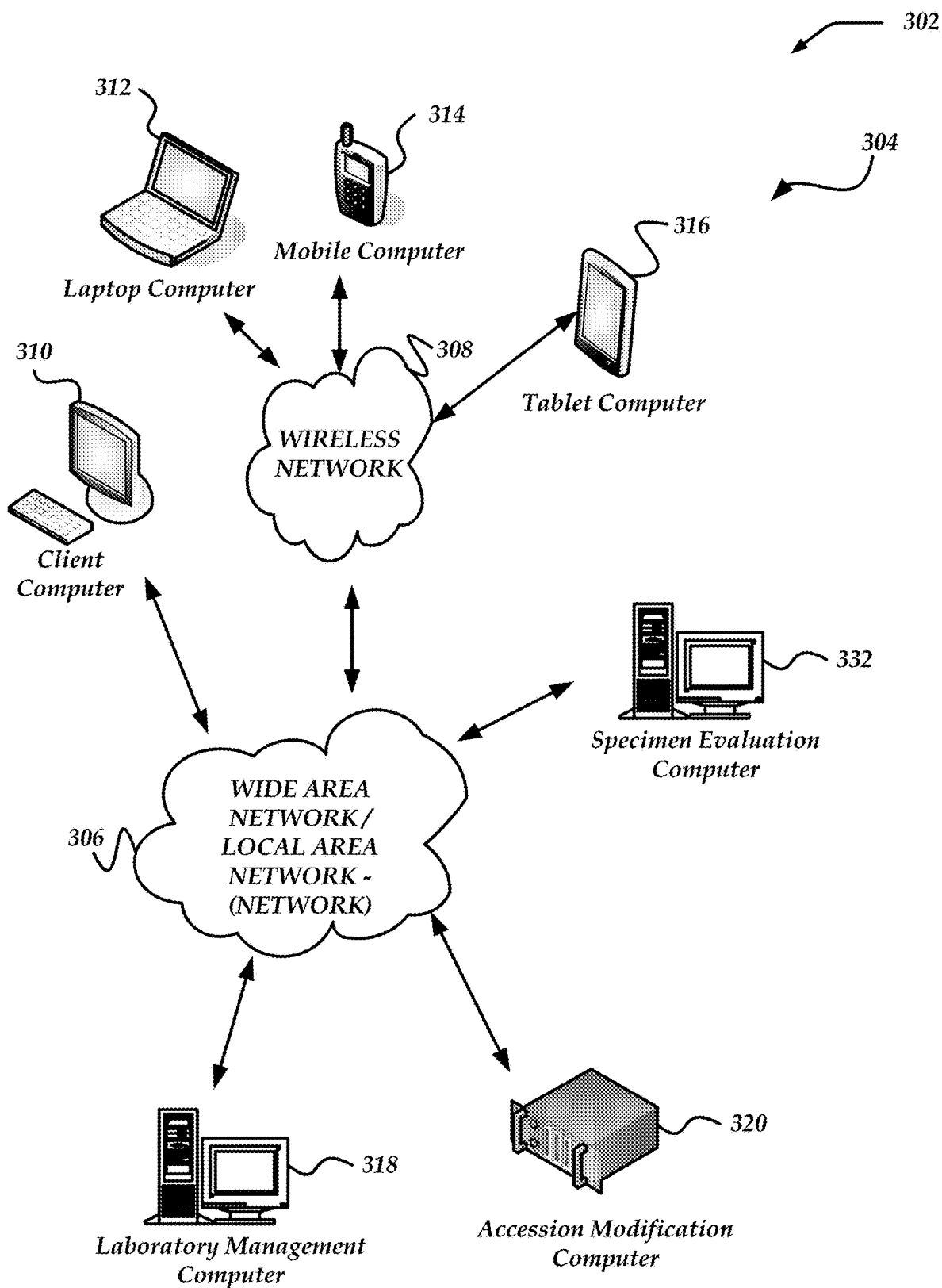
FIG. 8 illustrates a schematic representation of a system environment in which the system of FIG. 1 is implemented according to some embodiments.

FIG. 8 shows components of an environment 302 in which a system 304 of the invention is practiced according to some embodiments. As shown, the environment 302 of FIG. 8 includes local area networks (LANs)/wide area networks (WANs)—(network) 306, wireless network 308, client computers 310, 312, 314, 316, laboratory management computer 318, accession modification computer 320, specimen evaluation computer 332, or others.

Figure 9:
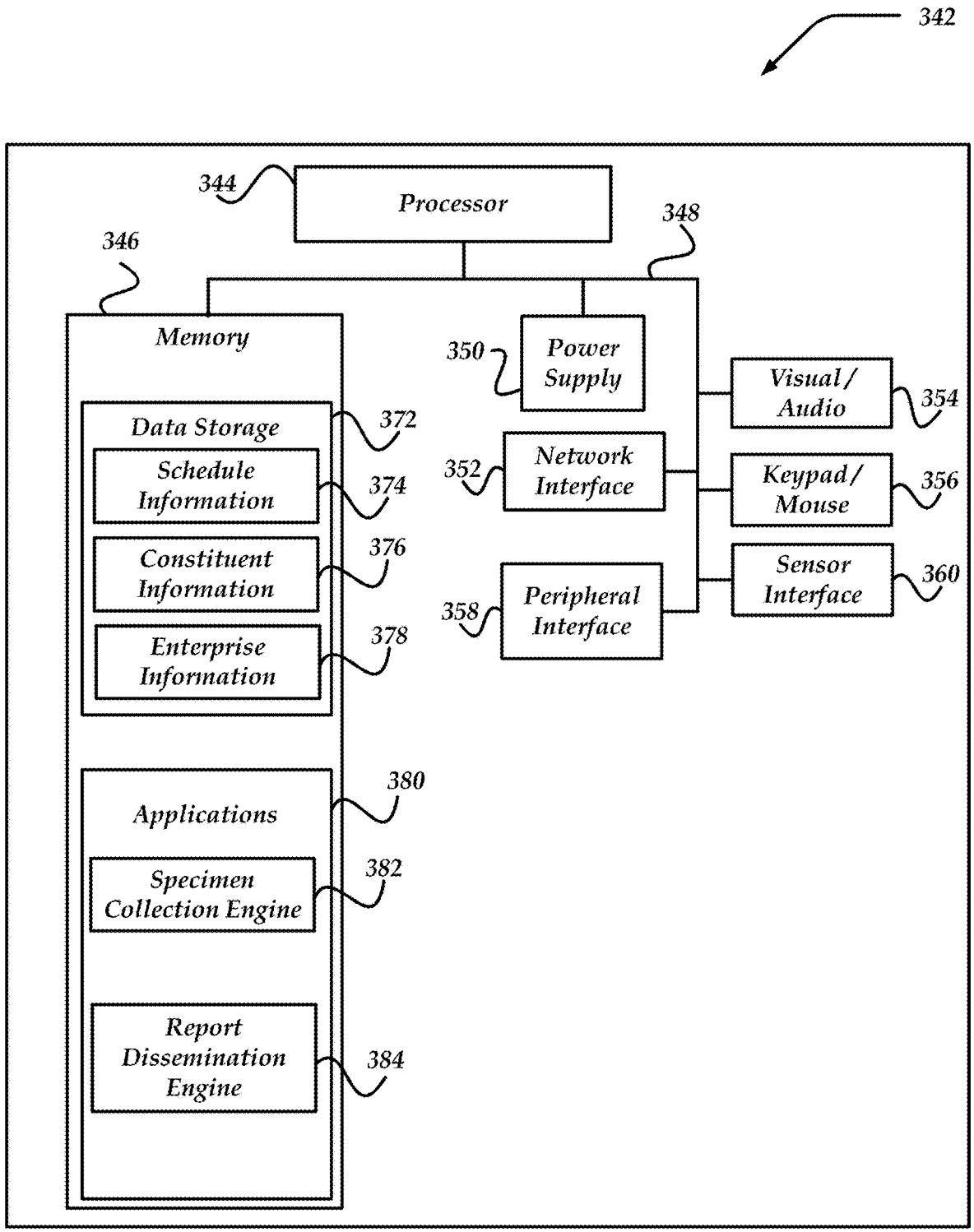
FIG. 9 shows a schematic representation of a client computer of the system of FIG. 1 according to some embodiments.

An embodiment of the client computers 310-316 is described with respect to FIG. 9. In some embodiments, one or more of the client computers 310-316 operate over one or more wired or wireless networks, such as the networks 306, 308. In some embodiments, one or more of the client computers 310-316 are configured to operate within a business or other entity to perform a variety of services for the business or other entity. In some embodiments, one or more of the client computers 310-316 are implemented as or executing respective ones of the enterprise clients 8, 12 of FIG. 1. In some embodiments, one or more of the client computers 310-316 are operated by respective constituents of the enterprises 6, 10. In some embodiments, the client computers 310-316 include one or more other client applications that are configured to facilitate providing information or receiving information from the engines of FIG. 1, such as providing the information provided with collected specimens that the laboratory management engine 16 gathers when accessioning current specimens or such as receiving medical-test or diagnosis reports.

Figure 10:
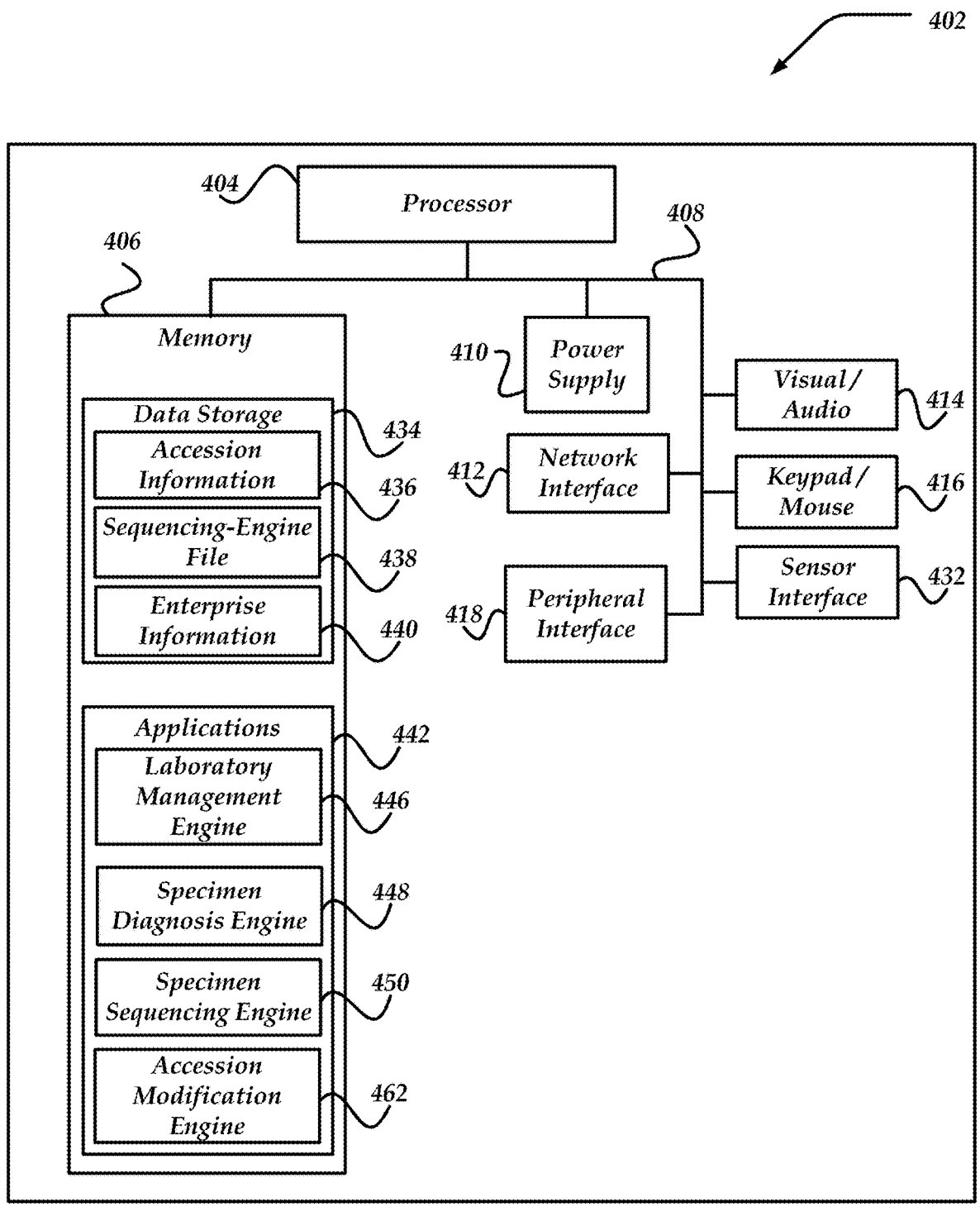
FIG. 10 illustrates a schematic representation of a network computer of the system of FIG. 1 according to some embodiments.

One embodiment of the laboratory management computer 318, the accession modification computer 320, or the specimen evaluation computer 332 is described with respect to FIG. 10. Briefly, however, each respective one or more of the laboratory management computer 318, the accession modification computer 320, or the specimen evaluation computer 332 is, in some embodiments, configured to implement one or more of the engines of FIG. 1 to implement or execute one or more portions of the processes described herein. In particular, in some embodiments, one or more of the laboratory management computer 318, the accession modification computer 320, or the specimen evaluation computer 332, alone or in combination, facilitate securely and efficiently providing medical-test or diagnostic reports to enterprises or patients for current specimens collected from such patients without personal information being collected with the current specimens.

Although FIG. 8 illustrates the laboratory management computer 318, the accession modification computer 320, or the specimen evaluation computer 332 each as a single computer, one or more of the laboratory management computer 318, the accession modification computer 320, or the specimen evaluation computer 332 in some embodiments are distributed across one or more distinct network computers. Moreover, in one or more embodiments, one or more of the laboratory management computer 318, the accession modification computer 320, or the specimen evaluation computer 332 are implemented using one or more cloud instances in one or more cloud networks, as shown in FIG. 1.

FIG. 9 schematically shows one embodiment of a client computer 342 that represents, in some embodiments, one or more of the client computers 310-316 in FIG. 8. In some embodiments, the client computer 342 includes a processor 344 in communication with memory 346 via bus 348. In some embodiments, the client computer 342 has a power supply 350, network interface 352, visual or audio interface 354 (e.g., one or more of a display screen, microphone, or speaker) to facilitate presenting reports generated by the system 2 of FIG. 1 or providing instructions for collection of specimens or personal information, controls such as a keypad or mouse 356 to manually enter personal information from a patient with collection of biological specimens from such patient, a peripheral interface 358 to facilitate gathering information from external peripheral devices such as specimen collection devices, or a sensor interface 360 (e.g., employee or student identification or badge scanner to facilitate collecting personal information from such employee or student when collecting biological specimens from such patient).

In some embodiments, the memory 346 includes data storage 372, which stores one or more portions of schedule information 374 (e.g., schedules for batch specimen collection; schedules for employee shifts or student attendance), constituent information 376 (e.g., employee numbers or student identification numbers associating constituents of an enterprise with such enterprise), or enterprise information 378 (e.g., name or contact information for the enterprise 6, 10 in FIG. 1). In some embodiments, the memory 346 includes applications 380, such as one or more of a specimen collection engine 382 or a report dissemination engine 384. In some embodiments, the specimen collection engine 382 facilitates collecting one or more of specimens from patients or personal information in connection with such specimens, as described with respect to the enterprise clients of FIG. 1, such as with peripheral devices connected to the client computer 342 by the peripheral interface 358 or the sensor interface 360. In some embodiments, the report dissemination engine 384 facilitates the client computer 342 obtaining medical-test or diagnosis reports, alerts, or other notifications generated by the system 2 to facilitate disseminating such information to appropriate personnel or patients at the enterprise associated with the client computer 342. In some embodiments, one or more of the applications are executed as or in a web browser.

FIG. 10 schematically shows one embodiment of a network computer 402 that represents, in some embodiments, one or more of the network computers 318, 320, 332 in FIG. 8. In some embodiments, the network computer 402 includes a processor 404 in communication with memory 406 via bus 408. In some embodiments, the client computer 402 has a power supply 410, network interface 412, visual or audio interface 414 (e.g., one or more of a display screen, microphone, or speaker) to facilitate presenting accession information or current specimen information in the system 2 of FIG. 1 to laboratory technicians facilitating medical tests or diagnoses or providing instructions for such tests or diagnoses, controls such as a keypad or mouse 416 to manually enter results of evaluations or medical tests or diagnoses based on current specimens, a peripheral interface 418 to facilitate gathering information from external peripheral devices such as specimen evaluation devices discussed above with respect to specimen diagnosis engine 20 or specimen sequencing engine 34 (e.g., laboratory equipment to facilitate medical evaluation or diagnosis or to facilitate genetic sequencing or fingerprinting), or a sensor interface 432 (e.g., container scanner to facilitate tracking containers of current specimens throughout the testing or diagnosis process or the sequencing process).

In some embodiments, the memory 406 includes data storage 434, which stores one or more portions of accession information 436 (e.g., the accession file 48 of FIG. 2), sequencing-engine file as discussed with respect to one or more of processes 122, 172, 222, or 252, or enterprise information 440 (e.g., name or contact information for the enterprises 6, 10 in FIG. 1). In some embodiments, the memory 406 includes applications 442, such as one or more of a laboratory management engine 446, a specimen diagnosis engine 448, a specimen sequencing engine 450, or an accession modification engine 462. In some embodiments, the specimen sequencing engine 450 and the accession modification engine 462 are implemented by separate and distinct computers that cannot access the other of the specimen sequencing engine 450 or the accession modification engine 462 to promote isolation between such engines and thus further isolation between the patient database 36 and the specimen database 36. In some embodiments, one or more of the engines 446, 448, 450, or 462 are configured in the manner described with respect to one or more of the similarly named engines 16, 18, 20, 22, 32, or 34 of FIG. 1. In some embodiments, the laboratory management computer 318 of FIG. 8 has or executes the laboratory management engine 446, the specimen evaluation computer 332 of FIG. 8 has or executes one or more of the specimen diagnosis engine 448 or the specimen sequencing engine, or the accession modification computer 320 of FIG. 8 has or executes the accession modification engine 462. In some embodiments, one or more of the engines shown in FIG. 10 perform their respective functions by utilizing one or more peripheral devices connected to the network computer 402 by the peripheral interface 418 or the sensor interface 432 or by accessing databases (e.g., the patient database 36 or the specimen database 40) through the network interface 412. In some embodiments, the network computer 402 collects the personal information or provides the medical-test or diagnosis results or reports to the client computer 342 of FIG. 9 through the network interface 412, which in some embodiments, interfaces with the applications 380 in the client computer 342 through the network interface 352 of the client computer 342.

In some embodiments, one or more of the applications 380 or 442 are separate and discrete from one or more of each other. In some embodiments, one or more of the applications 380 or 442 include one or more portions of one or more others of the applications 380 or 442. In some embodiments, one or more of the applications 380 or 442 are implemented as modules or components of another application. Further, in some embodiments, one or more of applications 380 or 442 are implemented as operating system extensions, modules, plugins, or others.

In some embodiments, one or more portions of the applications 380 or 442 are operative in a cloud-based computing environment. In some embodiments, the engines execute within virtual machines or virtual servers that are managed in a cloud-based based computing environment. In some embodiments in this context of cloud-based computing, the applications flow from one physical network computer within the cloud-based environment to another depending on performance and scaling considerations automatically managed by the cloud computing environment. In some embodiments, virtual machines or virtual servers dedicated to one or more of the applications 380 or 442 are provisioned and de-commissioned automatically. Also, in some embodiments, one or more of the applications 380 or 442 are located in virtual servers running in a cloud-based computing environment rather than being tied to one or more specific physical network computers. In some embodiments, one or more of the applications 380 or 442 individually or cooperatively perform one or more portions of one or more of the actions described herein, such as one or more actions associated with one or more blocks in one or more of the processes described herein. In some embodiments, one or more of the named engines have sub-engines (not shown) that individually or cooperatively perform one or more portions of the one or more actions. In some embodiments, one or more of the named engines are included as part of another one or more of the named engines.

In some embodiments, network computer 402 has a hardware security module (HSM) for providing additional tamper resistant safeguards for generating, storing or using security/cryptographic information, such as keys, digital certificates, passwords, passphrases, two-factor authentication information, or others to facilitate exclusive access or credentials to a database to which another network computer lacks access, such as a respective one of the patient database 36 or the specimen database 40. In some embodiments, hardware security module is employed to support one or more standard public key infrastructures (PKI) and is employed to generate, manage, or store keys pairs, or others. In some embodiments, HSM is a stand-alone network computer, and in other cases, HSM is arranged as a hardware card that is installable in the network computer 402.

All of the patents, published applications, and non-patent literature referred to in this specification or listed in the information disclosure statement filed herewith are incorporated herein by reference in their entirety, except to the extent that they are inconsistent with the disclosure of this application.

As used herein, the following terms take the meanings explicitly associated herein, unless the context clearly dictates otherwise. The terms "bearing" or "affixed" in the context of an identifier with respect to a container refers to identifiers that the container has or can have thereon before collection of a specimen held in the specimen (i.e., as used herein, a specimen can be collected, contained, or held in a container, but the container cannot bear or have affixed thereto a specimen). The terms "personally identifiable information", "personally identifying information", or "personal information" as used herein refer to information that (individually or in combination) enables uniquely identifying an individual with respect to other constituents of the same enterprise as the individual, wherein such enterprise includes at least 100 individual constituents. The term "configured" as used herein means an element being one or more of programmed, networked, sized, dimensioned, positioned, oriented, or otherwise modified to achieve or provide the recited function or result. The term "or" is an inclusive grammatical conjunction to indicate that one or more of the connected terms may be employed. For example, the phrase "one or more A, B, or C" or the phrase "one or more As, Bs, or Cs" is employed to discretely disclose each of the following: i) one or more As, ii) one or more Bs, iii) one or more Cs, iv) one or more As and one or more Bs, v) one or more As and one or more Cs, vi) one or more Bs and one or more Cs, and vii) one or more As, one or more Bs, and one or more Cs. The term "based on" as used herein is not exclusive and allows for being based on additional factors not described. The articles "a," "an," and "the" include plural references. Plural references are intended to also disclose the singular.

While the preferred embodiment of the invention has been illustrated and described, as noted above, many changes can be made without departing from the spirit and scope of the invention. For example, each disclosure of a component preferably having a feature or characteristic is intended to also disclose the component as being devoid of that feature or characteristic, unless the principles of the invention clearly dictate otherwise. Accordingly, the scope of the invention is not limited by the disclosure of the preferred embodiment. Instead, the invention should be determined entirely by reference to the claims that follow. It should also be noted that the claim dependencies or combinations of elements recited in the claims does not reflect an intention to forgo claiming other subject matter disclosed herein. Instead, this disclosure is intended to also disclose the subject matter of any combination of any two or more of the claims, such that subsequent claim sets may recite that any one of the dependent claims depends from any other one or more claims, up to and including all other claims in the alternative (for example, "The apparatus or method of any one of the preceding or subsequent claims . . . "). This disclosure is also intended to disclose the subject matter of any one of the dependent claims, as if it was an independent claim, with or without all or a portion of the subject matter of the original independent claim(s) or any other subject matter disclosed herein.

The invention claimed is:

1. A method for facilitating securely and efficiently providing medical-test results, the method comprising:
receiving first personally identifiable information for a first patient with a first biological specimen collected from the first patient, the first biological specimen being received in a first container that bears a first container identifier;
storing the first personally identifiable information for the first patient and the first container identifier in a first record of a first database;
evaluating the first biological specimen to generate genetic values representative of the first biological specimen;
storing the generated genetic values representative of the first biological specimen and the first container identifier in a first record of a second database;
evaluating the first biological specimen to generate a result of a first medical test, wherein the first biological specimen is tracked during the first medical test based on the first container identifier;
transmitting the result of the first medical test based on the first personally identifiable information for the first patient;
receiving a second biological specimen collected from the first patient, the second biological specimen being received in a second container that bears a second container identifier and without personally identifiable information for the first patient, wherein the second container does not bear the first container identifier and does not have affixed thereon personally identifiable information of the first patient;
evaluating the second biological specimen to generate genetic values representative of the second biological specimen;
matching a portion of the genetic values representative of the second biological specimen with a portion of the genetic values representative of the first biological specimen in the first record of the second database;
obtaining the first container identifier from the first record of the second database based on matching the portion of the genetic values representative of the second biological specimen with the portion of the genetic values representative of the first biological specimen in the first record of the second database;
evaluating the second biological specimen to generate a result of a second medical test, wherein the second biological specimen is tracked during the second medical test based on the second container identifier;
linking the result of the second medical test with the first personally identifiable information in the first record of the first database based on a match between the first container identifier obtained from the first record of the second database with the first container identifier in the first record of the first database;
transmitting the result of the second medical test based on the first personally identifiable information obtained based on the link,
whereby the first container identifier facilitates increasing security by enabling storage of the first personally identifiable information separate from the genetic values representative of the first biological specimen and facilitates providing the result of the second medical test to the first patient without the first patient providing personally identifiable information with the second biological sample.

2. The method of claim 1, wherein the first database is stored on a first computing system and requires first credentials to access the first record of the first database, the second database is stored on a second computing system and requires second credentials to access the first record of the second database, the first record of the first database is not accessible with the second credentials, the first record of the second database is not accessible with the first credentials, and the first and second computing systems are isolated from each other.

3. The method of claim 1, wherein the genetic values representative of the first biological specimen and the genetic values representative of the second biological specimen provide a DNA fingerprint.

4. The method of claim 1, wherein transmitting the result of the second medical test includes generating and transmitting a test report that includes the result of the second medical test and the first personally identifiable information obtained based on the link.

5. The method of claim 1, wherein the first database requires first credentials to access the first record of the first database, the second database requires second credentials to access the first record of the second database, the first record of the first database is not accessible with the second credentials, and the first record of the second database is not accessible with the first credentials.

6. The method of claim 1, wherein the first database is a patient information database, the second database is a specimen identifier database, the first database is stored on a first computing system, the second database is stored on a second computing system, and the first and second computing systems are isolated from each other.

7. The method of claim 1, wherein the first database is housed at a first geographic location, and the second database is housed at a second geographic location that is separate and distinct from the first geographic location.

8. The method of claim 1, wherein first container identifier is encoded in a machine-readable identifier affixed to the first container.

9. The method of claim 1, wherein the values representative of the first biological specimen and the values representative of the second biological specimen provide a DNA fingerprint.

10. The method of claim 1, wherein the first database includes multiple records that each associate a respective identifier in a plurality of linking identifiers with personal information for a respective patient in a plurality of patients, and wherein the second database includes multiple records that each associate one of the linking identifiers with values representative of a respective biological specimen in a plurality of biological specimens collected from respective patients in the plurality of patients.

11. The method of claim 10, wherein the linking identifiers are values encoded on containers used to collect biological specimens from the patients prior to storing the linking identifiers in the first database, the values representative of the biological specimens are DNA fingerprints of the biological specimens, and each container used to collect biological specimens from the patients after storing the linking identifiers in the first database is devoid of the linking identifier and does not have personally identifying information affixed thereto.

12. The method of claim 1, further comprising:
based on evaluation of a third biological specimen collected from a second patient, obtaining values representative of the third biological specimen with second personal information for the second patient;
determining that at least a portion of the values representative of the third biological specimen match at least a portion of values representative of the first biological specimen collected from the first patient; and
based on the match with at least the portion of the values representative of the third biological specimen, transmitting an alert.

13. A method for facilitating securely and efficiently providing medical-test results, the method comprising:
receiving first personally identifiable information for a first patient with a first biological specimen collected from the first patient, the first biological specimen being received in a first container that bears a first container identifier;
storing the first personally identifiable information for the first patient and a first link in a first record of a first database;
evaluating the first biological specimen to generate genetic values representative of the first biological specimen;
storing the generated genetic values representative of the first biological specimen and the first link in a first record of a second database;
evaluating the first biological specimen to generate a result of a first medical test, wherein the first biological specimen is tracked during the first medical test based on the first container identifier;
transmitting the result of the first medical test based on the first personally identifiable information for the first patient;
receiving a second biological specimen collected from the first patient, the second biological specimen being received in a second container that bears a second container identifier and without personally identifiable information for the first patient, wherein the second container does not bear the first container identifier, does not bear the first link, and does not have affixed thereon personally identifiable information of the first patient;
evaluating the second biological specimen to generate genetic values representative of the second biological specimen;
matching a portion of the genetic values representative of the second biological specimen with a portion of the genetic values representative of the first biological specimen in the first record of the second database;
obtaining the first link from the first record of the second database based on matching the portion of the genetic values representative of the second biological specimen with the portion of the genetic values representative of the first biological specimen in the first record of the second database;
evaluating the second biological specimen to generate a result of a second medical test, wherein the second biological specimen is tracked during the second medical test based on the second container identifier;
linking the result of the second medical test with the first personally identifiable information in the first record of the first database based on a match between the first link obtained from the first record of the second database with the first link in the first record of the first database;
transmitting the result of the second medical test based on the first personally identifiable information obtained based on the linking of the result of the second medical test with the first personally identifiable information,
whereby the first link facilitates increasing security by enabling storage of the first personally identifiable information separate from the genetic values representative of the first biological specimen and facilitates providing the result of the second medical test to the first patient without the first patient providing personally identifiable information with the second biological sample.

14. The method of claim 13, wherein the genetic values representative of the first biological specimen and the genetic values representative of the second biological specimen provide a DNA fingerprint.

15. The method of claim 13, wherein transmitting the result of the second medical test includes generating and transmitting a test report that includes the result of the second medical test and the first personally identifiable information obtained based on the link.

16. The method of claim 13, wherein the first database requires first credentials to access the first record of the first database, the second database requires second credentials to access the first record of the second database, the first record of the first database is not accessible with the second credentials, and the first record of the second database is not accessible with the first credentials.

17. The method of claim 13, wherein the first database is a patient information database, the second database is a specimen identifier database, the first database is stored on a first computing system, the second database is stored on a second computing system, and the first and second computing systems are isolated from each other.

18. The method of claim 13, wherein the first database includes multiple records that each associate a respective identifier in a plurality of linking identifiers with personal information for a respective patient in a plurality of patients, and wherein the second database includes multiple records that each associate one of the linking identifiers with values representative of a respective biological specimen in a plurality of biological specimens collected from respective patients in the plurality of patients.

19. The method of claim 18, wherein the linking identifiers are values encoded on containers used to collect biological specimens from the patients prior to storing the linking identifiers in the first database, the values representative of the biological specimens are DNA fingerprints of the biological specimens, and each container used to collect biological specimens from the patients after storing the linking identifiers in the first database is devoid of the linking identifier and does not have personally identifying information affixed thereto.

20. The method of claim 13, wherein first link as stored in the first record of the first database is encrypted or first part of an encryption key pair, and the first link as stored in the first record of the second database is encrypted or a second part of the key pair.

* * * * *